(12) United States Patent
Nicolaides et al.

(10) Patent No.: US 7,759,121 B2
(45) Date of Patent: *Jul. 20, 2010

(54) METHODS FOR GENERATING HYPERMUTABLE YEAST

(75) Inventors: Nicholas C. Nicolaides, Boothwyn, PA (US); Philip M. Sass, Audubon, PA (US); Luigi Grasso, Philadelphia, PA (US); Bert Vogelstein, Baltimore, MD (US); Kenneth W. Kinzler, Bel Air, MD (US)

(73) Assignees: The John Hopkins University, Baltimore, MD (US); Morphotek, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/930,400

(22) Filed: Oct. 31, 2007

(65) Prior Publication Data

US 2008/0176329 A1 Jul. 24, 2008

Related U.S. Application Data

(60) Continuation of application No. 11/188,743, filed on Jul. 26, 2005, which is a continuation of application No. 10/641,068, filed on Aug. 15, 2003, now Pat. No. 6,921,666, which is a division of application No. 09/788,657, filed on Feb. 21, 2001, now Pat. No. 6,656,736.

(60) Provisional application No. 60/184,336, filed on Feb. 23, 2000.

(51) Int. Cl.
*C12N 15/01* (2006.01)

(52) U.S. Cl. .................. 435/441; 435/447; 435/448; 435/462; 435/455; 435/483

(58) Field of Classification Search ................. None
See application file for complete search history.

(56) References Cited

U.S. PATENT DOCUMENTS

| | | | | |
|---|---|---|---|---|
| 5,587,290 | A | * | 12/1996 | Klionsky et al. ............... 435/6 |
| 5,907,079 | A | | 5/1999 | Mak et al. |
| 6,146,894 | A | | 11/2000 | Nicolaides et al. |
| 6,191,268 | B1 | | 2/2001 | Liskay et al. |
| 6,287,862 | B1 | | 9/2001 | delCardayre et al. |
| 6,656,736 | B2 | * | 12/2003 | Nicolaides et al. .......... 435/483 |
| 6,921,666 | B2 | * | 7/2005 | Nicolaides et al. .......... 435/483 |

FOREIGN PATENT DOCUMENTS

| | | |
|---|---|---|
| CA | 2240609 | 10/1999 |
| WO | WO 97/08312 | 3/1997 |
| WO | WO 99/19492 | 4/1999 |

OTHER PUBLICATIONS

Allen, D., et al., "MutS mediates heteroduplex loop formation by a translocation mechanism" *EMBO J., 1997*, 16(14), 4467-4476.

Baker, S.M., et al., "Male mice defective in the DNA mismatch repair gene PMS2 exhibit abnormal chromosome synapsis in meiosis" *Cell*, 1995, 82, 309-319.

Bronner C.E., et al., "Mutation in the DNA mismatch repair gene homologue hMLH1 is associated with hereditary non-polyposis colon cancer" *Nature*, 1994, 368, 258-261.

de Wind, N., et al., "Inactivation of the mouse Msh2 gene results in mismatch repair deficiency, methylation tolerance, hyperrecombination, and predisposition to cancer" *Cell*, 1995, 82, 321-330.

Drummond, J.T., et al., "Isolation of an hMSH2-p160 heterodimer that restores DNA mismatch repair to tumor cells" *Science*, 1995, 268, 1909-1912.

Drummond, J.T., et al., "Cisplatin and adriamycin resistance are associated with mutlα and mismatch repair deficiency in an ovarian tumor cell line" *J. Biological Chemistry*, 1996, 271(33), 19645-19648.

Edelmann, W., et al., "Meiotic pachytene arrest in MLH1-deficient mice" *Cell*, 1996, 85, 1125-1134.

Eshleman, J.R., et al., "Mismatch repair defects in human carcinogenesis" *Human Molecular Genetics*, 1996, 5, 1489-1494.

Galio, L., et al., "ATP hydrolysis-dependent formation of a dynamic ternary nucleoprotein complex with MutS and MutL" *Nucleic Acids Research*, 1999, 27(11), 2325-2331.

Hamilton, S.R. et al. "The molecular basis of Turcot's syndrome." *N. Eng. J. Med*. 1995, 332:839-847.

Harfe, B.D., "DNA mismatch repair and genetic instability" *Annu. Rev. Genet.*, 2000, 34, 359-399.

Hoang J., et al., "BAT-26, an Indicator of the Replication Error Phenotype in Colorectal Cancers and Cell Lines" *Cancer Res.*, 1997, 57, 300-303.

Holmes, J., S. Clark, and P. Modrich. "Strand-specific mismatch correction in nuclear extracts of human and *Drosophila melanogaster* cell lines" *Proc. Natl. Acad. Sci.* USA 1990 87:5837-5841.

Honma, M. et al., "Cytotoxic and Mutagenic Responses to X-rays and Chemical Mutagens in Normal and p53-mutated Human Lymphoblastoid Cells" *Mut. Res.*, 1997, 374, 89-98.

Jiricny, J., et al., "Mismatch repair defects in cancer" *Curr. Opin. Genet. Dev.*, 2000, 10, 157-161.

Karran, P., et al., "Genomic instability and tolerance to alkylating agents" *Cancer Surveys*, 1996, 28, 69-71.

Leach, F.S., et al., "Mutations of a mutS homolog in hereditary nonpolyposis colorectal cancer" *Cell*, 1993, 75, 1215-1225.

Li, G.-M. and P. Modrich. "Restoration of mismatch repair to nuclear extracts of H6 colorectal tumor cells by a heterodimer of human MutL homologs" *Proc. Natl. Acad. Sci.* USA 1995 92:1950-1954.

(Continued)

*Primary Examiner*—James S Ketter
(74) *Attorney, Agent, or Firm*—Banner & Witcoff, Ltd

(57) ABSTRACT

Yeast cells are mutagenized to obtain desirable mutants. Mutagenesis is mediated by a defective mismatch repair system which can be enhanced using conventional exogenously applied mutagens. Yeast cells with the defective mismatch repair system are hypermutable, but after selection of desired mutant yeast strains, they can be rendered genetically stable by restoring the mismatch repair system to proper functionality.

22 Claims, No Drawings

OTHER PUBLICATIONS

Liu, T., et al., "Microsatellite instability as a predictor of a mutation in a DNA mismatch repair gene in familial colorectal cancer" *Genes, Chromosomes & Cancer*, 2000, 27, 17-25.

Nicolaides et al., "A Naturally Occurring hPMS2 Mutation Can Confer a Dominant Negative Mutator Pehnotype", *Molecular and Cellular Biology*, vol. 18, No.3, (Mar. 1988), pp. 1635-1641.

Liu et al., "Analysis of Mismatch Repair Genes in Hereditary Non-polyposis Colorectal Cancer Patients" *Nature Medicine*, Feb. 1996, 2(2), 169-174.

Ma et al., "Dominant Negative Expression of hPMS2 Creates Isogenic Mismatch Repair Deficient Human Colon Cancer Cell Lines" *Proc. Am. Assoc. Cancer Res.*, Mar. 1998, 39, p. 460 (Abstract #3130).

McCallum, C.M., "Targeted screening for induced mutations" *Nature Biotechnology*, 2000, 18, 455-457.

Modrich, P., "Mismatch repair, genetic stability, and cancer" *Science*, 1994, 266, 1959-1960.

Nicolaides, N.C., et al., "The jun family members, c-jun and junD, transactivate the human c-*myb*, promotor via an Ap1-like element" *J. Biological Chemistry*, 1992, 267(27), 19655-19672.

Nicolaides, N.C., et al., "Genomic organization of the human *PMS2* gene family" *Genomics*, 1995, 30, 195-206.

Nicolaides, N.C. et al. "Molecular cloning of the N-terminus of GTBP." *Genomics* 1996, 31:395-397.

Nicolaides, N.C., et al., "Positive autoregulation of c-*myb*, expression via Myb binding sites in the 5' flanking region of the human c-*myb* gene" *Molecular and Cellular Biology*, 1991, 11(12), 6166-6176.

Nicolaides, N.C., et al., "Analysis of the 5' region of *PMS2* reveals heterogeneous transcripts and a novel overlapping gene" *Genomics*, 1995, 29, 329-334.

Nicolaides, N.C., et al., "Mutations of two PMS homologues in hereditary nonpolyposis colon cancer" *Nature*, 1994, 371, 75-80.

Palombo, F., et al., "Mismatch repair and cancer" *Nature*, 1994, 367, 417.

Pang, Q., T.A. Prolla and R.M. Liskay, "Functional domains of the *Saccharomyces cerevisiae* Mlh1p and Pms1p DNA mismatch repair proteins and their relevance to human hereditary nonpolyposis colorectal cancer-associated mutations" *Mol. Cell. Biol.* 1997 17(8):4465-4473.

Papadopoulos, N., et al., "Mutation of a *mutL* homolog in hereditary colon cancer" *Science*, 1994, 263, 1625-1629.

Papadopoulos, N., et al., "Mutations of *GTBP* in genetically unstable cells" *Science*, 1995, 268, 1915-1917.

Parsons, R. et al. "Mismatch repair deficiency in phenotypically normal human cells." *Science* 1995 268:738-740.

Parsons, R., et al., "hypermutability and mismatch repair deficiency in RER+ tumor cells" *Cell*, 1993, 75, 1227-1236.

Peinado, M.A., et al., "Isolation and characterization of allelic losses and gains in colorectal tumors by arbitrarily primed polymerase chain reaction" *Proc. Natl. Acad. Sci.* USA, 1992, 89, 10065-10069.

Perucho, M., et al., "Cancer of the microsatellite mutator phenotype" *Biol. Chem.*, 1996, 377, 675-684.

Prolla, T.A., et al., "MLH1, PMS1, and MSH2 interactions during the initiation of DNA mismatch repair in yeast" *Science*, 1994, 265, 1091-1093.

Quian, Y. et al., "Molecular events after antisense inhibition of hMSH2 in a HeLa cell line" *Mutation Research*, Oct. 12, 1998, vol. 418, pp. 61-71.

Spampinato, C., et al., "The MutL ATPase is required for mismatch repair" *J. Biological Chemistry*, 2000, 275(13), 9863-9869.

Strand, M., et al., "Destabilization of tracts of simple repetitive DNA in yeast by mutations affecting DNA mismatch repair" *Nature*, 1993, 365, 274-276.

Su, S., et al., "Mispair specificity of methyl-directed DNA mismatch correction in vitro" *J. Biological Chemistry*, 1988, 263(14), 6829-6835.

Vora, K.A. et al., "Severe Attenuation of the B Cell Immune Response in Msh2-deficient Mice" *Journal of Experimental Medicine*, Feb. 1999, 189(3), 471-481.

Wheeler, J.M.D., et al., "The role of hypermethylation of the *hMLH*1 promoter region in HNPCC verus MSI=sporadic colorectal cancers" *J. Med. Genet.*, 2000, 588-592.

Winter, D.B. et al., "Altered spectra of hypermutation in antibodies from mice deficient for the DNA mismatch repair protein PMS2" *Proc. Natl. Acad. Sci.*, USA, Jun. 1998, 95, 6953-6958.

Polaczek et al., "Functional genetic tests of DNA mismatch repair protein activity in *Saccharomyces cerevisiae*", *Gene*, vol. 213, (1998), pp. 159-167.

Aronshtam et al., "Dominant negative mutator mutations in the mutL gene of *Escherichia coli*", *Nucleic Acids Research*, (1996), vol. 24, No. 13, pp. 2498-2504.

Cascalho et al., "Mismatch Repair Co-opted by Hypermutation", *Science*, vol. 279, (Feb. 1998), pp. 1207-1210.

Studamire et al, Mol. Cell. Biol., vol. 19(11), pp. 7558-7567 (1999).

Alani et al, Mol. Cell. Biol., vol. 17, pp. 2436-2447 (1997).

Bell et al, Genomics, vol. 19, pp. 137-144 (1994).

Bjornson et al, Biochemistry, vol. 39, pp. 3176-3183 (2000).

Kong et al, Molecular Immunology, vol. 36, pp. 83-91 (1999).

Schrader et al, J. Exp. Med., vol. 190, pp. 323-330 (1999).

Fishel, R. et al. "The human mutator gene homolog MSH2 and its association with hereditary nonpolyposis colon cancer." *Cell* 1993, 7:1027-1038.

* cited by examiner

METHODS FOR GENERATING HYPERMUTABLE YEAST

This application claims the benefit of provisional application Ser. No. 60/184,336 filed Feb. 23, 2000.

FIELD OF THE INVENTION

The invention is related to the area of mismatch repair genes. In particular it is related to the field of in situ mutagenesis of single celled organisms.

BACKGROUND OF THE INVENTION

Within the past four years, the genetic cause of the Hereditary Nonpolyposis Colorectal Cancer Syndrome (HNPCC), also known as Lynch syndrome II, has been ascertained for the majority of kindred's affected with the disease (Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169-174). The molecular basis of HNPCC involves genetic instability resulting from defective mismatch repair (MMR). To date, six genes have been identified in humans that encode for proteins and appear to participate in the MMR process, including the mutS homologs GTBP, hMSH2, and hMSH3 and the mutL homologs hMLH1, hPMS1, and hPMS2 (Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary non-polyposis colon cancer. Nature 368:258-261; Fishel, R., Lescoe, M., Rao, M. R. S., Copeland, N. J., Jenkins, N. A., Garber, J., Kane, M., and Kolodner, R. 1993. The human mutator gene homolog MSH2 and its association with hereditary nonpolyposis colon cancer. Cell 7:1027-1038; Leach, F. S., Nicolaides, N. C, Papadopoulos, N., Liu, B., Jen, J., Parsons, R., Peltomaki, P., Sistonen, P., Aaltonen, L. A., Nystrom-Lahti, M., Guan, X. Y., Zhang, J., Meltzer, P. S., Yu, J. W., Kao, F. T., Chen, D. J., Cerosaletti, K. M., Foumier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215-1225; Nicolaides, N. C., Papadopoulos, N., Liu, B., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and Kinzler, K. W. 1994. Mutations of two PMS homologs in hereditary nonpolyposis colon cancer. Nature 371: 75-80; Nicolaides, N. C., Palombo, F., Kinzler, K. W., Vogelstein, B., and Jiricny, J. 1996. Molecular cloning of the N-terminus of GTBP. Genomics 31:395-397; Palombo, F., Hughes, M., Jiricny, J., Truong, O., Hsuan, J. 1994. Mismatch repair and cancer. Nature 36:417; Palombo, F., Gallinari, P., Iaccarino, I., Lettieri, T., Hughes, M. A., Truong, O., Hsuan, J. J., and Jiricny, J. 1995. GTBP, a 160-kilodalton protein essential for mismatch-binding activity in human cells. Science 268:1912-1914; Papadopoulos, N., Nicolaides, N. C., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and Kinzler, K. W. 1994. Mutation of a mutL homolog is associated with hereditary colon cancer. Science 263:1625-1629). Germline mutations in four of these genes (hMSH2, hMLH1, hPMS1, and hPMS2) have been identified in HNPCC kindred's (Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary non-polyposis colon cancer. Nature 368:258-261; Leach, F. S., Nicolaides, N. C, Papadopoulos, N., Liu, B., Jen, J., Parsons, R., Peltomaki, P., Sistonen, P., Aaltonen, L. A., Nystrom-Lahti, M., Guan, X. Y., Zhang, J., Meltzer, P. S., Yu, J. W., Kao, F. T., Chen, D. J., Cerosaletti, K. M., Foumier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215-1225; Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169-174; Nicolaides, N. C., Papadopoulos, N., Liu, B., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and Kinzler, K. W. 1994. Mutations of two PMS homologs in hereditary non-polyposis colon cancer. Nature 371: 75-80; Papadopoulos, N., Nicolaides, N. C., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and Kinzler, K. W. 1994. Mutation of a mutL homolog is associated with hereditary colon cancer. Science 263:1625-1629). Though the mutator defect that arises from the MMR deficiency can affect any DNA sequence, microsatellite sequences are particularly sensitive to MMR abnormalities (Modrich, P. 1994. Mismatch repair, genetic stability, and cancer. Science 266:1959-1960). Microsatellite instability (MI) is therefore a useful indicator of defective MMR. In addition to its occurrence in virtually all tumors arising in HNPCC patients, MI is found in a small fraction of sporadic tumors with distinctive molecular and phenotypic properties (Perucho, M. 1996. Cancer of the microsatellite mutator phenotype. Biol. Chem. 377:675-684).

HNPCC is inherited in an autosomal dominant fashion, so that the normal cells of affected family members contain one mutant allele of the relevant MMR gene (inherited from an affected parent) and one wild-type allele (inherited from the unaffected parent). During the early stages of tumor development, however, the wild-type allele is inactivated through a somatic mutation, leaving the cell with no functional MMR gene and resulting in a profound defect in MMR activity. Because a somatic mutation in addition to a germ-line mutation is required to generate defective MMR in the tumor cells, this mechanism is generally referred to as one involving two hits, analogous to the biallelic inactivation of tumor suppressor genes that initiate other hereditary cancers (Leach, F. S., Nicolaides, N. C, Papadopoulos, N., Liu, B., Jen, J., Parsons, R., Peltomaki, P., Sistonen, P., Aaltonen, L. A., Nystrom- Lahti, M., Guan, X. Y., Zhang, J., Meltzer, P. S., Yu, J. W., Kao, F. T., Chen, D. J., Cerosaletti, K. M., Foumier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215-1225; Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169-174; Parsons, R., Li, G. M., Longley, M. J., Fang, W. H., Papadopolous, N., Jen, J., de la Chapelle, A., Kinzler, K. W., Vogelstein, B., and Modrich, P. 1993. Hypermutability and mismatch repair deficiency in RER+ tumor cells. Cell 75:1227-1236). In line with this two-hit mechanism, the non-neoplastic cells of HNPCC patients generally retain near normal levels of MMR activity due to the presence of the wild-type allele.

The ability to alter the signal transduction pathways by manipulation of a gene products function, either by over-expression of the wild type protein or a fragment thereof, or by introduction of mutations into specific protein domains of the protein, the so-called dominant-negative inhibitory mutant, were described over a decade in the yeast system *Saccharomyces cerevisiae* by Herskowitz (Nature 329(6136): 219-222, 1987). It has been demonstrated that over-expression of wild type gene products can result in a similar, dominant-negative inhibitory phenotype due most likely to the "saturating-out" of a factor, such as a protein, that is present at low levels and necessary for activity; removal of the protein by binding to a high level of its cognate partner results in the same net effect, leading to inactivation of the protein and the associated signal transduction pathway. Recently, work done by Nicolaides et. al. (Nicolaides N C, Littman S J, Modrich P, Kinzler K W, Vogelstein B 1998. A naturally occurring hPMS2 mutation can confer a dominant negative mutator phenotype. Mol Cell Biol 18:1635-1641) has demonstrated the utility of introducing dominant negative inhibitory mismatch repair mutants into mammalian cells to confer global DNA hypermutability. The ability to manipulate the MMR process and therefore increase the mutability of the target host genome at will, in this example a mammalian cell, allows for the generation of innovative cell subtypes or variants of the original wild type cells. These variants can be placed under a specified, desired selective process, the result of which is a novel organism that expresses an altered biological molecule(s) and has a new trait. The concept of creating and introducing dominant negative alleles of a gene, including the MMR alleles, in bacterial cells has been documented to result in genetically altered prokaryotic mismatch repair genes (Aronshtam A, Marinus M G. 1996. Dominant negative mutator mutations in the mutL gene of *Escherichia coli*. Nucleic Acids Res 24:2498-2504; Wu T H, Marinus M G. 1994. Dominant negative mutator mutations in the mutS gene of *Escherichia coli*. J Bacteriol 176:5393-400; Brosh R M Jr, Matson S W. 1995. Mutations in motif II of *Escherichia coli* DNA helicase II render the enzyme nonfunctional in both mismatch repair and excision repair with differential effects on the unwinding reaction. J Bacteriol 177:5612-5621). Furthermore, altered MMR activity has been demonstrated when MMR genes from different species including yeast, mammalian cells, and plants are over-expressed (Fishel, R., Lescoe, M., Rao, M. R. S., Copeland, N. J., Jenkins, N. A., Garber, J., Kane, M., and Kolodner, R. 1993. The human mutator gene homolog MSH2 and its association with hereditary nonpolyposis colon cancer. Cell 7:1027-1038; Studamire B, Quach T, Alani, E. 1998. *Saccharomyces cerevisiae* Msh2p and Msh6p ATPase activities are both required during mismatch repair. Mol Cell Biol 18:7590-7601; Alani E, Sokolsky T, Studamire B, Miret J J, Lahue R S. 1997. Genetic and biochemical analysis of Msh2p-Msh6p: role of ATP hydrolysis and Msh2p-Msh6p subunit interactions in mismatch base pair recognition. Mol Cell Biol 17:2436-2447; Lipkin S M, Wang V, Jacoby R, Banerjee-Basu S, Baxevanis A D, Lynch H T, Elliott R M, and Collins F S. 2000. MLH3: a DNA mismatch repair gene associated with mammalian microsatellite instability. Nat. Genet. 24:27-35).

There is a continuing need in the art for methods of genetically manipulating useful strains of yeast to increase their performance characteristics and abilities.

SUMMARY OF THE INVENTION

It is an object of the present invention to provide a method for rendering yeast cells hypermutable.

It is another object of the invention to provide hypermutable yeast cells.

It is a further object of the invention to provide a method of mutating a gene of interest in a yeast.

It is yet another object of the present invention to provide a method to produce yeast that are hypermutable.

It is an object of the invention to provide a method to restore normal mismatch repair activity to hypermutable cells following strain selection.

These and other objects of the invention are provided by one or more of the following embodiments. In one embodiment a method is provided for making a hypermutable yeast. A polynucleotide comprising a dominant negative allele of a mismatch repair gene is introduced into a yeast cell. The cell thus becomes hypermutable.

According to another embodiment a homogeneous composition of cultured, hypermutable yeast cells is provided. The yeast cells comprise a dominant negative allele of a mismatch repair gene.

According to still another embodiment of the invention a method is provided for generating a mutation in a gene of interest. A yeast cell culture comprising the gene of interest and a dominant negative allele of a mismatch repair gene is cultivated. The yeast cell is hypermutable. Cells of the culture are tested to determine whether the gene of interest harbors a mutation.

In yet another embodiment of the invention a method is provided for generating a mutation in a gene of interest. A yeast cell comprising the gene of interest and a polynucleotide encoding a dominant negative allele of a mismatch repair gene is grown to create a population of mutated, hypermutable yeast cells. The population of mutated, hypermutable yeast cells is cultivated under trait selection conditions. Yeast cells which grow under trait selection conditions are tested to determine whether the gene of interest harbors a mutation.

Also provided by the present invention is a method for generating enhanced hypermutable yeast. A yeast cell is exposed to a mutagen. The yeast cell is defective in mismatch repair (MMR) due to the presence of a dominant negative allele of at least one MMR gene. An enhanced rate of mutation of the yeast cell is achieved due to the exposure to the mutagen.

According to still another aspect of the invention a method is provided for generating mismatch repair (MMR)-proficient yeast with new output traits. A yeast cell comprising a gene of interest and a polynucleotide encoding a dominant negative allele of a mismatch repair gene is grown to create a population of mutated, hypermutable yeast cells. The population of mutated, hypermutable yeast cells is cultivated under trait selection conditions. The yeast cells which grow under trait selection conditions are tested to determine whether the gene of interest harbors a mutation. Normal mismatch repair activity is restored to the yeast cells.

These and other embodiments of the invention provide the art with methods that can generate enhanced mutability in yeast as well as providing single-celled eukaryotic organisms harboring potentially useful mutations to generate novel output traits for commercial applications.

DETAILED DESCRIPTION OF THE INVENTION

It is a discovery of the present invention that hypermutable yeast can be made by altering the activity of endogenous mismatch repair activity of host cells. Dominant negative alleles of mismatch repair genes, when introduced and expressed in yeast, increase the rate of spontaneous mutations by reducing the effectiveness of endogenous mismatch repair-mediated DNA repair activity, thereby rendering the yeast highly susceptible to genetic alterations, i.e., hypermutable. Hypermutable yeast can then be utilized to screen for mutations in a gene or a set of genes in variant siblings that exhibit an output trait(s) not found in the wild-type cells.

The process of mismatch repair, also called mismatch proofreading, is an evolutionarily highly conserved process that is carried out by protein complexes described in cells as disparate as prokaryotic cells such as bacteria to more complex mammalian cells (Modrich, P. 1994. Mismatch repair, genetic stability, and cancer. Science 266:1959-1960; Parsons, R., Li, G. M., Longley, M., Modrich, P., Liu, B., Berk, T., Hamilton, S. R., Kinzler, K. W., and Vogelstein, B. 1995. Mismatch repair deficiency in phenotypically normal human cells. Science 268:738-740; Perucho, M. 1996. Cancer of the microsatellite mutator phenotype. Biol. Chem. 377:675-684). A mismatch repair gene is a gene that encodes one of the proteins of such a mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base that is complementary to the older DNA strand. In this way, cells eliminate many mutations that occur as a result of mistakes in DNA replication, resulting in genetic stability of the sibling cells derived from the parental cell.

Some wild type alleles as well as dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134 (Parsons, R., Li, G. M., Longley, M., Modrich, P., Liu, B., Berk, T., Hamilton, S. R., Kinzler, K. W., and Vogelstein, B. 1995. Mismatch repair deficiency in phenotypically normal human cells. Science 268:738-740; Nicolaides N C, Littman S J, Modrich P, Kinzler K W, Vogelstein B 1998. A naturally occurring hPMS2 mutation can confer a dominant negative mutator phenotype. Mol Cell Biol 18:1635-1641). The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any mismatch repair allele, which produces such effect, can be used in this invention, whether it is wild-type or altered, whether it derives from mammalian, yeast, fungal, amphibian, insect, plant, or bacteria. In addition, the use of over-expressed wild type MMR gene alleles from human, mouse, plants, and yeast in bacteria has been shown to cause a dominant negative effect on the bacterial hosts MMR activity (Aronshtam A, Marinus M G. 1996. Dominant negative mutator mutations in the mutL gene of Escherichia coli. Nucleic Acids Res 24:2498-2504; Wu T H, Marinus M G. 1994. Dominant negative mutator mutations in the mutS gene of Escherichia coli. J Bacteriol 176:5393-400; Brosh R M Jr, Matson S W. 1995. Mutations in motif II of Escherichia coli DNA helicase II render the enzyme nonfunctional in both mismatch repair and excision repair with differential effects on the unwinding reaction. J Bacteriol 177:5612-5621; Lipkin S M, Wang V, Jacoby R, Banerjee-Basu S, Baxevanis A D, Lynch H T, Elliott R M, and Collins F S. 2000. MLH3: a DNA mismatch repair gene associated with mammalian microsatellite instability. Nat Genet. 24:27-35). This suggests that perturbation of the multi-component MMR protein complex can be accomplished by introduction of MMR components from other species into yeast.

Dominant negative alleles of a mismatch repair gene can be obtained from the cells of humans, animals, yeast, bacteria, plants or other organisms. Screening cells for defective mismatch repair activity can identify such alleles. Mismatch repair genes may be mutant or wild type. Yeast host MMR may be mutated or not. The term yeast used in this application comprises any organism from the eukaryotic kingdom, including but not limited to Saccharomyces sp., Pichia sp., Schizosaccharomyces sp., Kluyveromyces sp., and other fungi (Gellissen, G. and Hollenberg, C P. Gene 190(1):87-97, 1997). These organisms can be exposed to chemical mutagens or radiation, for example, and can be screened for defective mismatch repair. Genomic DNA, cDNA, mRNA, or protein from any cell encoding a mismatch repair protein can be analyzed for variations from the wild-type sequence. Dominant negative alleles of a mismatch repair gene can also be created artificially, for example, by producing variants of the hPMS2-134 allele or other mismatch repair genes (Nicolaides N C, Littman S J, Modrich P, Kinzler K W, Vogelstein B 1998. A naturally occurring hPMS2 mutation can confer a dominant negative mutator phenotype. Mol Cell Biol 18:1635-1641). Various techniques of site-directed mutagenesis can be used. The suitability of such alleles, whether natural or artificial, for use in generating hypermutable yeast can be evaluated by testing the mismatch repair activity (using methods described in Nicolaides N C, Littman S J, Modrich P, Kinzler K W, Vogelstein B 1998. A naturally occurring hPMS2 mutation can confer a dominant negative mutator phenotype. Mol Cell Biol 18:1635-1641) caused by the allele in the presence of one or more wild-type alleles to determine if it is a dominant negative allele.

A yeast that over-expresses a wild type mismatch repair allele or a dominant negative allele of a mismatch repair gene will become hypermutable. This means that the spontaneous mutation rate of such yeast is elevated compared to yeast without such alleles. The degree of elevation of the spontaneous mutation rate can be at least 2-fold, 5-fold, 10-fold, 20-fold, 50-fold, 100-fold, 200-fold, 500-fold, or 1000-fold that of the normal yeast as measured as a function of yeast doubling/hour.

According to one aspect of the invention, a polynucleotide encoding either a wild type or a dominant negative form of a mismatch repair protein is introduced into yeast. The gene can be any dominant negative allele encoding a protein which is part of a mismatch repair complex, for example, mutS, mutL, mutH, or mutY homologs of the bacterial, yeast, plant or mammalian genes (Modrich, P. 1994. Mismatch repair, genetic stability, and cancer. Science 266:1959-1960; Prolla, T. A, Pang, Q., Alani, E., Kolodner, R. A., and Liskay, R. M. 1994. MLH1, PMS1, and MSH2 Interaction during the initiation of DNA mismatch repair in yeast. Science 264:1091-1093). The dominant negative allele can be naturally occurring or made in the laboratory. The polynucleotide can be in the form of genomic DNA, cDNA, RNA, or a chemically synthesized polynucleotide or polypeptide. The molecule can be introduced into the cell by transformation, electroporation, mating, particle bombardment, or other method described in the literature.

Transformation is used herein as any process whereby a polynucleotide or polypeptide is introduced into a cell. The process of transformation can be carried out in a yeast culture using a suspension of cells. The yeast can be any type classified under the eukaryotic kingdom as by international convention.

In general, transformation will be carried out using a suspension of cells but other methods can also be employed as long as a sufficient fraction of the treated cells incorporate the polynucleotide or polypeptide so as to allow transfected cells to be grown and utilized. The protein product of the polynucleotide may be transiently or stably expressed in the cell. Techniques for transformation are well known to those skilled in the art. Available techniques to introduce a polynucleotide or polypeptide into a yeast cell include but are not limited to electroporation, viral transduction, cell fusion, the use of spheroplasts or chemically competent cells (e.g. calcium chloride), and packaging of the polynucleotide together with lipid for fusion with the cells of interest. Once a cell has been transformed with the mismatch repair gene or protein, the cell can be propagated and manipulated in either liquid culture or on a solid agar matrix, such as a petri dish. If the transfected cell is stable, the gene will be expressed at a consistent level for many cell generations, and a stable, hypermutable yeast strain results.

An isolated yeast cell can be obtained from a yeast culture by chemically selecting strains using antibiotic selection of an expression vector. If the yeast cell is derived from a single cell, it is defined as a clone. Techniques for single-cell cloning of microorganisms such as yeast are well known in the art.

A polynucleotide encoding a dominant negative form of a mismatch repair protein can be introduced into the genome of yeast or propagated on an extra-chromosomal plasmid, such as the 2-micron plasmid. Selection of clones harboring a mismatch repair gene expression vector can be accomplished by plating cells on synthetic complete medium lacking the appropriate amino acid or other essential nutrient as described (J. C. Schneider and L. Guarente, Methods in Enzymology 194:373, 1991). The yeast can be any species for which suitable techniques are available to produce transgenic microorganisms, such as but not limited to genera including *Saccharomyces, Schizosaccharomyces, Pichia, Hansenula, Kluyveromyces* and others.

Any method for making transgenic yeast known in the art can be used. According to one process of producing a transgenic microorganism, the polynucleotide is introduced into the yeast by one of the methods well known to those in the art. Next, the yeast culture is grown under conditions that select for cells in which the polynucleotide encoding the mismatch repair gene is either incorporated into the host genome as a stable entity or propagated on a self-replicating extra-chromosomal plasmid, and the protein encoded by the polynucleotide fragment transcribed and subsequently translated into a functional protein within the cell. Once transgenic yeast is engineered to harbor the expression construct, it is then propagated to generate and sustain a culture of transgenic yeast indefinitely.

Once a stable, transgenic yeast cell has been engineered to express a defective mismatch repair (MMR) protein, the yeast can be cultivated to create novel mutations in one or more target gene(s) of interest harbored within the same yeast cell. A gene of interest can be any gene naturally possessed by the yeast or one introduced into the yeast host by standard recombinant DNA techniques. The target gene(s) may be known prior to the selection or unknown. One advantage of employing such transgenic yeast cells to induce mutations in resident or extra-chromosomal genes within the yeast is that it is unnecessary to expose the cells to mutagenic insult, whether it is chemical or radiation, to produce a series of random gene alterations in the target gene(s). This is due to the highly efficient nature and the spectrum of naturally occurring mutations that result as a consequence of the altered mismatch repair process. However, it is possible to increase the spectrum and frequency of mutations by the concomitant use of either chemical and/or radiation together with MMR defective cells. The net effect of the combination treatment is an increase in mutation rate in the genetically altered yeast that are useful for producing new output traits. The rate of the combination treatment is higher than the rate using only the MMR-defective cells or only the mutagen with wild-type MMR cells.

MMR-defective yeast of the invention can be used in genetic screens for the direct selection of variant sub-clones that exhibit new output traits with commercially desirable applications. This permits one to bypass the tedious and time consuming steps of gene identification, isolation and characterization.

Mutations can be detected by analyzing the internally and/or externally mutagenized yeast for alterations in its genotype and/or phenotype. Genes that produce altered phenotypes in MMR-defective microbial cells can be discerned by any of a variety of molecular techniques well known to those in the art. For example, the yeast genome can be isolated and a library of restriction fragments of the yeast genome can be cloned into a plasmid vector. The library can be introduced into a "normal" cell and the cells exhibiting the novel phenotype screened. A plasmid can be isolated from those normal cells that exhibit the novel phenotype and the gene(s) characterized by DNA sequence analysis. Alternatively, differential messenger RNA screen can be employed utilizing driver and tester RNA (derived from wild type and novel mutant, respectively) followed by cloning the differential transcripts and characterizing them by standard molecular biology methods well known to those skilled in the art. Furthermore, if the mutant sought is encoded by an extra-chromosomal plasmid, then following co-expression of the dominant negative MMR gene and the gene of interest, and following phenotypic selection, the plasmid can be isolated from mutant clones and analyzed by DNA sequence analysis using methods well known to those in the art. Phenotypic screening for output traits in MMR-defective mutants can be by biochemical activity and/or a readily observable phenotype of the altered gene product. A mutant phenotype can also be detected by identifying alterations in electrophoretic mobility, DNA binding in the case of transcription factors, spectroscopic properties such as IR, CD, X-ray crystallography or high field NMR analysis, or other physical or structural characteristics of a protein encoded by a mutant gene. It is also possible to screen for altered novel function of a protein in situ, in isolated form, or in model systems. One can screen for alteration of any property of the yeast associated with the function of the gene of interest, whether the gene is known prior to the selection or unknown.

The screening and selection methods discussed are meant to illustrate the potential means of obtaining novel mutants with commercially valuable output traits, but they are not meant to limit the many possible ways in which screening and selection can be carried out by those of skill in the art.

Plasmid expression vectors that harbor a mismatch repair (MMR) gene insert can be used in combination with a number of commercially available regulatory sequences to control both the temporal and quantitative biochemical expression level of the dominant negative MMR protein. The regulatory sequences can be comprised of a promoter, enhancer or promoter/enhancer combination and can be inserted either upstream or downstream of the MMR gene to control the expression level. The regulatory sequences can be any of those well known to those in the art, including but not limited to the AOX1, GAP, GAL1, GAL10, PHO5, and PGK promoters harbored on high or low copy number extra-chromosomal expression vectors or on constructs that are integrated into the genome via homologous recombination. These types of regulatory systems have been disclosed in scientific publications and are familiar to those skilled in the art.

Once a microorganism with a novel, desired output trait of interest is created, the activity of the aberrant MMR activity is desirably attenuated or eliminated by any means known in the art. These include but are not limited to removing an inducer from the culture medium that is responsible for promoter activation, curing a plasmid from a transformed yeast cell, and addition of chemicals, such as 5-fluoro-orotic acid to "loop-out" the gene of interest.

In the case of an inducibly controlled dominant negative MMR allele, expression of the dominant negative MMR gene will be turned on (induced) to generate a population of hypermutable yeast cells with new output traits. Expression of the dominant negative MMR allele can be rapidly turned off to reconstitute a genetically stable strain that displays a new output trait of commercial interest. The resulting yeast strain is now useful as a stable strain that can be applied to various commercial applications, depending upon the selection process placed upon it.

In cases where genetically deficient mismatch repair yeast [strains such as but not limited to: M1 (mutS) and in EC2416 (mutS delta umuDC), and mutL or mutY strains] are used to derive new output traits, transgenic constructs can be used that express wild type mismatch repair genes sufficient to complement the genetic defect and therefore restore mismatch repair activity of the host after trait selection [Grzesiuk, E. et. al. (Mutagenesis 13; 127-132, 1998); Bridges, B. A., et. al. (EMBO J. 16:3349-3356, 1997); LeClerc, J. E., Science 15:1208-1211, 1996); Jaworski, A. et. al. (Proc. Natl. Acad. Sci. USA 92:11019-11023, 1995)]. The resulting yeast is genetically stable and can be employed for various commercial applications.

The use of over-expression of foreign (exogenous, transgenic) mismatch repair genes from human and yeast such as MSH2, MLH1, MLH3, etc. have been previously demonstrated to produce a dominant negative mutator phenotype in yeast hosts (Shcherbakova, P. V., Hall, M. C., Lewis, M. S., Bennett, S. E., Martin, K. J., Bushel, P. R., Afshari, C. A., and Kunkel, T. A. Mol. Cell. Biol. 21(3):940-951; Studamire B, Quach T, Alani, E. 1998. *Saccharomyces cerevisiae* Msh2p and Msh6p ATPase activities are both required during mismatch repair. Mol Cell Biol 18:7590-7601; Alani E, Sokolsky T, Studamire B, Miret J J, Lahue R S. 1997. Genetic and biochemical analysis of Msh2p-Msh6p: role of ATP hydrolysis and Msh2p-Msh6p subunit interactions in mismatch base pair recognition. Mol Cell Biol 17:2436-2447; Lipkin S M, Wang V, Jacoby R, Banerjee-Basu S, Baxevanis A D, Lynch H T, Elliott R M, and Collins F S. 2000. MLH3: a DNA mismatch repair gene associated with mammalian microsatellite instability. Nat Genet. 24:27-35). In addition, the use of yeast strains expressing prokaryotic dominant negative MMR genes as well as hosts that have genomic defects in endogenous MMR proteins have also been previously shown to result in a dominant negative mutator phenotype (Evans, E., Sugawara, N., Haber, J. E., and Alani, E. Mol. Cell. 5(5):789-799, 2000; Aronshtam A, Marinus M G. 1996. Dominant negative mutator mutations in the mutL gene of *Escherichia coli*. Nucleic Acids Res 24:2498-2504; Wu T H, Marinus M G. 1994. Dominant negative mutator mutations in the mutS gene of *Escherichia coli*. J Bacteriol 176:5393-400; Brosh R M Jr, Matson S W. 1995. Mutations in motif II of *Escherichia coli* DNA helicase II render the enzyme nonfunctional in both mismatch repair and excision repair with differential effects on the unwinding reaction. J Bacteriol 177:5612-5621). However, the findings disclosed here teach the use of MMR genes, including the human PMSR2 gene (Nicolaides, N. C., Carter, K. C., Shell, B. K., Papadopoulos, N., Vogelstein, B., and Kinzler, K. W. 1995. Genomic organization of the human PMS2 gene family. Genomics 30:195-206), the related PMS134 truncated MMR gene (Nicolaides N. C., Kinzler, K. W., and Vogelstein, B. 1995. Analysis of the 5' region of PMS2 reveals heterogenous transcripts and a novel overlapping gene. Genomics 29:329-334), the plant mismatch repair genes (U.S. patent application Ser. No. 09/749,601) and those genes that are homologous to the 134 N-terminal amino acids of the PMS2 gene to create hypermutable yeast.

DNA mutagens can be used in combination with MMR defective yeast hosts to enhance the hypermutable production of genetic alterations. This further reduces MMR activity and is useful for generation of microorganisms with commercially relevant output traits.

The ability to create hypermutable organisms using dominant negative alleles can be used to generate innovative yeast strains that display new output features useful for a variety of applications, including but not limited to the manufacturing industry, for the generation of new biochemicals, for detoxifying noxious chemicals, either by-products of manufacturing processes or those used as catalysts, as well as helping in remediation of toxins present in the environment, including but not limited to polychlorobenzenes (PCBs), heavy metals and other environmental hazards. Novel yeast strains can be selected for enhanced activity to either produce increased quantity or quality of a protein or non-protein therapeutic molecule by means of biotransformation. Biotransformation is the enzymatic conversion of one chemical intermediate to the next intermediate or product in a pathway or scheme by a microbe or an extract derived from the microbe. There are many examples of biotransformation in use for the commercial manufacturing of important biological and chemical products, including penicillin G, erythromycin, and clavulanic acid. Organisms that are efficient at conversion of "raw" materials to advanced intermediates and/or final products also can perform biotransformation (Berry, A. Trends Biotechnol. 14(7):250-256). The ability to control DNA hypermutability in host yeast strains using a dominant negative MMR (as described above) allows for the generation of variant subtypes that can be selected for new phenotypes of commercial interest, including but not limited to organisms that are toxin-resistant, have the capacity to degrade a toxin in situ or the ability to convert a molecule from an intermediate to either an advanced intermediate or a final product. Other applications using dominant negative MMR genes to produce genetic alteration of yeast hosts for new output traits include but are not limited to recombinant production strains that produce higher quantities of a recombinant polypeptide as well as the use of altered endogenous genes that can transform chemical or catalyze manufacturing downstream processes. A regulatable dominant negative MMR phenotype can be used to produce a yeast strain with a commercially beneficial output trait. Using this process, single-celled yeast cells expressing a dominant negative MMR can be directly selected for the phenotype of interest. Once a selected yeast with a specified output trait is isolated, the hypermutable activity of the dominant negative MMR allele can be turned-off by several methods well known to those skilled in the art. For example, if the dominant-negative allele is expressed by an inducible promoter system, the inducer can be removed or depleted. Sych systems include but are not limited to promoters such as: lactose inducibleGALi-GAL10 promoter (M. Johnston and R. W. Davis, *Mol. Cell Biol.* 4:1440, 1984); the phosphate inducible PHO5 promoter (A. Miyanohara, A. Toh-e, C. Nosaki, F. Nosaki, F. Hamada, N. Ohtomo, and K. Matsubara. *Proc. Natl. Acad. Sci. U.S.A.* 80:1, 1983); the alcohol dehydrogenase I (ADH) and 3-phosphoglycerate kinase (PGK) promoters, that are considered to be constitutive but can be repressed/de-repressed when yeast cells are grown in non-fermentable carbon sources such as but not limited to lactate (G. Ammerer, *Methods in Enzymology* 194: 192, 1991; J. Mellor, M. J. Dobson, N. A. Roberts, M. F. Tuite, J. S. Emtage, S. White, D. A. Lowe, T. Patel, A. J. Kingsman, and S. M. Kingsman, Gene 24:563, 1982); S. Hahn and L. Guarente, Science 240:317, 1988); Alcohol oxidase (AOX) in *Pichia pastoris* (Tschopp, J F, Brust, P F, Cregg, J M, Stillman, C A, and Gingeras, T R. Nucleic Acids Res. 15(9):3859-76, 1987; and the thiamine repressible expression promoter nmt1 in Schizosaccharomyces pombe (Moreno, M B, Duran, A., and Ribas, J C. Yeast 16(9):861-72, 2000). Yeast cells can be transformed by any means known to those skilled in the art, including chemical transformation with LiCl (Mount, R. C., Jordan, B. E., and Hadfield, C. Methods Mol. Biol. 53:139-145,1996) and electroporation (Thompson, J R, Register, E., Curotto, J., Kurtz, M. and Kelly, R. Yeast 14(6):565-71, 1998). Yeast cells that have been transformed with DNA can be selected for growth by a variety of methods, including but not restricted to selectable markers (URAS3; Rose, M., Grisafi, P., and Botstein, D. Gene 29:113,1984; LEU2; A. Andreadis, Y., Hsu, M., Hermodson, G., Kohlhaw, and P. Schimmel. J. Biol. Chem. 259:8059,1984; ARG4; G. Tschumper and J. Carbon. Gene 10:157, 1980; and HIS3; K. Struhl, D. T. Stinchcomb, S., Scherer, and R. W. Davis Proc. Natl. Acad. Sci. U.S.A. 76:1035,1979) and drugs that inhibit growth of yeast cells (tunicamycin, TUN; S. Hahn, J., Pinkham, R. Wei, R., Miller, and L. Guarente. Mol. Cell Biol. 8:655, 1988). Recombinant DNA can be introduced into yeast as described above and the yeast vectors can be harbored within the yeast cell either extra-chromosomally or integrated into a specific locus. Extra-chromosomal based yeast expression vectors can be either high copy based (such as the 2-μm vector Yep13; A. B. Rose and J. R. Broach, Methods in Enzymology 185:234,1991), low copy centromeric vectors that contain autonomously replicating sequences (ARS) such as YRp7 (M. Fitzgerald-Hayes, L. Clarke, and J. Carbon, Cell 29:235,1982) and well as integration vectors that permit gene of interest to be introduced into specified locus within the host genome and propagated in a stable manner (R. J. Rothstein, Methods in Enzymology 101:202, 1991). Ectopic expression of MMR genes in yeast can be attenuated or completely eliminated at will by a variety of methods, including but not limited to removal from the medium of the specific chemical inducer (e.g deplete galactose that drives expression of the GAL10 promoter in *Saccharomyces cerevisiae* or methanol that drives expression of the AOX1 promoter in *Pichia pastoris*), extra-chromosomally replicating plasmids can be "cured" of expression plasmid by growth of cells under non-selective conditions (e.g. Yep13 harboring cells can be propagated in the presence of leucine,) and cells that have genes inserted into the genome can be grown with chemicals that force the inserted locus to "loop-out" (e.g., integrants that have URA3 can be selected for loss of the inserted gene by growth of integrants on 5-fluoro-orotic acid (J. D. Boeke, F. LaCroute and G. R. Fink. Mol. Gen. Genet. 197:345-346, 1984). Whether by withdrawal of inducer or treatment of yeast cells with chemicals, removal of MMR expression results in the re-establishment of a genetically stable yeast cell-line. Thereafter, the lack of mutant MMR allows the endogenous, wild type MMR activity in the host cell to function normally to repair DNA. The newly generated mutant yeast strains that exhibit novel, selected output traits are suitable for a wide range of commercial processes or for gene/protein discovery to identify new biomolecules that are involved in generating a particular output trait. While it has been documented that MMR deficiency can lead to as much as a 1000-fold increase in the endogenous DNA mutation rate of a host, there is no assurance that MMR deficiency alone will be sufficient to alter every gene within the DNA of the host bacterium to create altered biochemicals with new activity(s). Therefore, the use of chemical mutagens and their respective analogues such as ethidium bromide, EMS, MNNG, MNU, Tamoxifen, 8-Hydroxyguanine, as well as others such as those taught in: Khromov-Borisov, N. N., et. al. (Mutat. Res. 430:55-74, 1999); Ohe, T., et. al. (Mutat. Res. 429:189-199, 1999); Hour, T. C. et. al. (Food Chem. Toxicol. 37:569-579, 1999); Hrelia, P., et. al. (Chem. Biol. Interact. 118:99-111, 1999); Garganta, F., et. al. (Environ. Mol. Mutagen. 33:75-85, 1999); Ukawa-Ishikawa S., et. al. (Mutat. Res. 412:99-107, 1998); the website having the URL address: www host server, ehs.utah.edu domain name, ohh directory, mutagens subdirectory etc. can be used to further enhance the spectrum of mutations and increase the likelihood of obtaining alterations in one or more genes that can in turn generate host yeast with a desired new output trait(s). Mismatch repair deficiency leads to hosts with an increased resistance to toxicity by chemicals with DNA damaging activity. This feature allows for the creation of additional genetically diverse hosts when mismatch defective yeast are exposed to such agents, which would be otherwise impossible due to the toxic effects of such chemical mutagens [Colella, G., et. al. (Br. J. Cancer 80:338-343, 1999); Moreland, N. J., et. al. (Cancer Res. 59:2102-2106, 1999); Humbert, O., et. al. (Carcinogenesis 20:205-214, 1999); Glaab, W. E., et. al. (Mutat. Res. 398:197-207, 1998)]. Moreover, mismatch repair is responsible for repairing chemically-induced DNA adducts, therefore blocking this process could theoretically increase the number, types, mutation rate and genomic alterations of a yeastl [Rasmussen, L. J. et. al. (Carcinogenesis 17:2085-2088, 1996); Sledziewska-Gojska, E., et. al. (Mutat. Res. 383:31-37, 1997); and Janion, C. et. al. (Mutat. Res. 210:15-22, 1989)]. In addition to the chemicals listed above, other types of DNA mutagens include ionizing radiation and UV-irradiation, which is known to cause DNA mutagenesis in yeast, can also be used to potentially enhance this process (Lee C C, Lin H K, Lin J K. 1994. A reverse mutagenicity assay for alkylating agents based on a point mutation in the beta-lactamase gene at the active site serine codon. Mutagenesis 9:401-405; Vidal A, Abril N, Pueyo C. 1995. DNA repair by Ogt alkyltransferase influences EMS mutational specificity. Carcinogenesis 16:817-821). These agents, which are extremely toxic to host cells and therefore result in a decrease in the actual pool size of altered yeast cells are more tolerated in MMR defective hosts and in turn permit an enriched spectrum and degree of genomic mutagenesis.

The above disclosure generally describes the present invention. A more complete understanding can be obtained by reference to the following specific examples that will be provided herein for purposes of illustration only, and are not intended to limit the scope of the invention.

EXAMPLES

Example 1

Generation of Inducible MMR Dominant Negative Allele Vectors and Yeast Cells Harboring the Expression VECTORS Yeast expression constructs were prepared to determine if the human PMS2 related gene (hPMSR2) (Nicolaides et al. Genomics 30(2):195-206) and the human PMS134 gene (Nicolaides N C, Littman S J, Modrich P, Kinzler K W, Vogelstein B 1998. A naturally occurring hPMS2 mutation can confer a dominant negative mutator phenotype. Mol Cell Biol 18:1635-1641) are capable of inactivating the yeast MMR activity and thereby increase the overall frequency of genomic hypermutation, a consequence of which is the generation of variant sib cells with novel output traits following host selection. For these studies, a plasmid encoding the hPMS134 cDNA was altered by polymerase chain reaction (PCR). The 5' oligonucleotide has the following structure: 5'-ACG CAT ATG GAG CGA GCT GAG AGC TCG AGT-3' (SEQ ID NO: 1) that includes the NdeI restriction site CAT ATG. The 3'-oligonucleotide has the following structure: 5'-GAA TTC TTA TCA CGT AGA ATC GAG ACC GAG GAG AGG GTT AGG GAT AGG CTT ACC AGT TCC AAC CTT CGC CGA TGC-3' (SEQ ID NO: 2) that includes an EcoRI site GAA TTC and the 14 amino acid epitope for the V5 antibody. The oligonucleotides were used for PCR under standard conditions that included 25 cycles of PCR (95° C. for 1 minute, 55° C. for 1 minute, 72° C. for 1.5 minutes for 25 cycles followed by 3 minutes at 72° C.). The PCR fragment was purified by gel electrophoresis and cloned into pTA2.1 (Invitrogen) by standard cloning methods (Sambrook et al., Molecular Cloning: A Laboratory Manual, Third Edition, 2001), creating the plasmid pTA2.1-hPMS134. pTA2.1-hPMS134 was digested with the restriction enzyme EcoRI to release the insert which was cloned into EcoRI restriction site of pPIC3.5K (Invitrogen). The following strategy, similar to that described above to clone human PMS134, was used to construct an expression vector for the human related gene PMSR2. First, the hPMSR2 fragment was amplified by PCR to introduce two restriction sites, an NdeI restriction site at the 5'- end and an Eco RI site at the 3'-end of the fragment. The 5'-oligonucleotide that was used for PCR has the following structure: 5'-ACG CAT ATG TGT CCT TGG CGG CCT AGA-3' (SEQ ID NO: 3) that includes the NdeI restriction site CAT ATG. The 3'-oligonucleotide used for PCR has the following structure: 5'-GAA TTC TTA TTA CGT AGA ATC GAG ACC GAG GAG AGG GTT AGG GAT AGG CTT ACC CAT GTG TGA TGT TTC AGA GCT-3' (SEQ ID NO: 4) that includes an EcoRI site GAA TTC and the V5 epitope to allow for antibody detection. The plasmid that contained human PMSR3 in pBluescript SK (Nicolaides et al. Genomics 30 (2):195-206,1995) was used as the PCR target with the hPMS2-specific oligonucleotides above. Following 25 cycles of PCR (95° C. for 1 minute, 55° C. for 1 minute, 72° C. for 1.5 minutes for 25 cycles followed by 3 minutes at 72° C.). The PCR fragment was purified by gel electrophoresis and cloned into pTA2.1 (Invitrogen) by standard cloning methods (Sambrook et al., Molecular Cloning: A Laboratory Manual, Third Edition, 2001), creating the plasmid pTA2.1-hR2. pTA2.1-hR2 was next digested with the restriction enzyme EcoRI to release the insert (there are two EcoRI restriction sites in the multiple cloning site of pTA2.1 that flank the insert) and the inserted into the yeast expression vector pPIC3.5K (Invitrogen).

*Pichia pastoris* yeast cells were transformed with pPIC3.5K vector, pPIC3.5K-pms134, and pPIC3.5K-hR2 as follows. First, 5 ml of YPD (1% yeast extract, 2% bacto-peptone, 1% dextrose) medium was inoculated with a single colony from a YPD plate (same as YPD liquid but add 2% difco-agar to plate) and incubated with shaking overnight at 30° C. The overnight culture was used to inoculate 500 ml of YPD medium (200 ul of overnight culture) and the culture incubated at 30° C. until the optical density at 600 nm reached 1.3 to 1.5. The cells were then spun down (4000×g for 10 minutes), and then washed 2 times in sterile water (one volume each time), then the cells suspended in 20 ml of 1M sorbitol. The sorbitol/cell suspension was spun down (4,000×g for 10 minutes) and suspended in 1 ml of 1M sorbitol. 80 ul of the cell suspension was mixed with 5 to 10 ug of linearized plasmid DNA and placed in a 0.2 cm cuvette, pulsed length 5 to 10 milliseconds at field strength of 7,500V/cm. Next, the cells are diluted in 1 ml of 1M sorbitol and transferred to a 15 ml tube and incubated at 30° C. for 1 to 2 hours without shaking. Next, the cells are spun out (4,000×G for 10 minutes) and suspended in 100 ul of sterile water, and 50 ul/plate spread onto the appropriate selective medium plate. The plates are incubated for 2 to 3 days at 30° C. and colonies patched out onto YPD plates for further testing.

Example 2

Generation of Hypermutable Yeast with Inducible Dominant Negative Alleles of Mismatch Repair Genes Yeast clones expressing human PMS2 homologue PMS-R2 or empty vector were grown in BMG (100 mM potassium phosphate, pH 6.0, 1.34% YNB (yeast nitrogen base), $4\times10^{-5}$% biotin, 1% glycerol) liquid culture for 24 hr at 30° C. The next day, cultures were diluted 1:100 in MM medium (1.34% YNB, $4\times10^{-5}$% biotin, 0.5% methanol) and incubated at 30° C. with shaking. Cells were removed for mutant selection at 24 and 48 hours post methanol induction as described below (see EXAMPLE 3).

Example 3

Dominant Negative MMR Genes can Produce New Genetic Variants and Commercially Viable Output Traits in Yeast The ability to express MMR genes in yeast, as presented in example 2, demonstrate the ability to generate genetic alterations and new phenotypes in yeast expressing dominant negative MMR genes. In this example we teach the utility of this d to create eukaryotic strains with commercially relevant output traits.

Generation of Uracil Dependent Yeast Strain

One example of utility is the generation of a yeast strain that is mutant for a particular metabolic product, such as an amino acid or nucleotide. Engineering such a yeast strain will allow for recombinant manipulation of the yeast strain for the introduction of genes for scalable process of recombinant manufacturing. In order to demonstrate that MMR can be manipulated in yeast to generate mutants that lack the ability to produce specific molecular building blocks, the following experiment was performed. Yeast cells that express a methanol inducible human PMS2 homologue, hPMS2-R2 (as described in example 1 above), were grown in BMY medium overnight then diluted 1:100 and transferred to MM medium, which results in activation of the AOX promoter and production of the hPMS2-R2 MMR gene that is resident within the yeast cell. Control cells were treated the same manner; these cells contain the pPIC3.5 vector in yeast and lack an insert. Cells were induced for 24 and 48 hours and then selected for uracil requiring mutations as follows. The cells were plated to 5-FOA medium (Boeke, J. D., LaCroute, F., and Fink, G. R. Mol. Gen. Genet. 197:345-345, 1984). The plates are made as follows: (2× concentrate (filter sterilize): yeast nitrogen base 7 grams; 5-fluoro-orotic acid 1 gram; uracil 50 milligrams; glucose 20 grams; water to 500 ml; Add to 500 ml 4% agar (autoclaved) and pour plates. Cells are plated on 5-FOA plates (0, 24 and 48 hour time points) and incubated at 30° C. for between 3 and 5 days. Data from a typical experiment is shown in Table 1. No uracil requiring clones were observed in the un-induced or induced culture in yeast cells that harbor the "empty" vector whereas those cells that harbor the MMR gene hPMS2-R2 have clones that are capable of growth on the selection medium. Note that the un-induced culture of hPMS2-R2 does not have any colonies that are resistant to 5-FOA, demonstrating that the gene must be induced for the novel phenotype to be generated. It has been demonstrated that the mutagens (such as ethyl methyl sulfonate result in a low number of ura$^-$ mutants and that the spontaneous mutation rate for generating this class of mutants is low (Boeke, J. D., LaCroute, F. and Fink, G. R. Mol. Gen. Genet. 197:345-346, 1984).

TABLE 1

Generation of uracil requiring mutant *Pichia pastoris* yeast cells.

| Strain | Seeded | ura$^-$ | URA$^+$ | Frequency (ura$^-$ cells) |
|---|---|---|---|---|
| Wt | 100,000 | 0 | ~100,000 | 0 |
| Empty | 100,000 | 0 | ~100,000 | 0 |
| pMOR$^{ye-1\#}$ | 100,000 | 14 | ~100,000 | 1/7,142 |
| pMOR$^{ye2@}$ | 100,000 | 123 | ~100,000 | 1/813 |
| Wt | 100,000 | 1-0.1 | 100,000 | 1/10$^{5-6}$* |
| Mutagen | 100,000 | 10 | 100,000 | 1/10,000 |

Represents at 24 hour methanol induction and @ a 48 hour induction. For comparison a wild type yeast cell treated/un-treated is shown (Galli, A. and Schiestl, R. H. Mutat. Res. 429(1): 13-26, 1999).

Generation of Heat-Resistant Producer Strains

One example of commercial utility is the generation of heat-resistant recombinant protein producer strains. In the scalable process of recombinant manufacturing, large-scale fermentation of both prokaryotes and eukaryotes results in the generation of excessive heat within the culture. This heat must be dissipated by physical means such as using cooling jackets that surround the culture while it is actively growing and producing product. Production of a yeast strain that can resist high temperature growth effectively would be advantageous for large-scale recombinant manufacturing processes. To this end, the yeast strain as described in EXAMPLE 2 can be grown in the presence of methanol to induce the dominant negative MMR gene and the cells grown for various times (e.g. 12, 24, 36 and 48 hours) then put on plates and incubated at elevated temperatures to select for mutants that resist high temperature growth (e.g. 37° C. or 42° C.). These strains would be useful for fermentation development and scale-up of processes and should result in a decrease in manufacturing costs due to the need to cool the fermentation less often.

Generation of High Recombinant Protein Producer Strains and Strains with Less Endogenous Protease Activity Yeast is a valuable recombinant-manufacturing organism since it is a single celled organism that is inexpensive to grow and easily lends itself to fermentation at scale. Further more, many eukaryotic proteins that are incapable of folding effectively when expressed in *Escherichia coli* systems fold with the proper conformation in yeast and are structurally identical to their mammalian counterparts. There are several inherent limitations of many proteins that are expressed in yeast including over and/or inappropriate glycosylation of the recombinant protein, proteolysis by endogenous yeast enzymes and insufficient secretion of recombinant protein from the inside of the yeast cell to the medium (which facilitates purification). To generate yeast cells that with this ability to over-secrete proteins, or with less endogenous protease activity and or less hyper-glycosylation activity yeast cells as described in example 1 can be grown with methanol for 12, 24, 36 and 48 hours and yeast cells selected for the ability to over-secrete the protein or interest, under-glycosylate it or a cell with attenuated of no protease activity. Such a strain will be useful for recombinant manufacturing or other commercial purposes and can be combined with the heat resistant strain outlined above. For example, a mutant yeast cell that is resistant to high temperature growth and can secrete large amounts of protein into the medium would result.

Similar results were observed with other dominant negative mutants such as the PMSR2, PMSR3, and the human MLH1 proteins.

Example 4

Mutations Generated in the Host Genome of Yeast by Defective MMR are Genetically Stable As described in example 3 manipulation of the MMR pathway in yeast results in alterations within the host genome and the ability to select for a novel output traits, for example the ability of a yeast cell to require a specific nutrient. It is important that the mutations introduced by the MMR pathway is genetically stable and passed to daughter cells reproducibly once the wild type MMR pathway is re-established. To determine the genetic stability of mutations introduced into the yeast genome the following experiment was performed. Five independent colonies from pPIC3.5K-hPMS2-R2 that are ura$^-$, five wild type control cells (URA$^+$) and five pPIC3.5K transformed cells ("empty vector") were grown overnight from an isolated colony in 5 ml of YPD (1% yeast extract, 2% bacto-peptone and 1% dextrose) at 30° C. with shaking. The YPD medium contains all the nutrients necessary for yeast to grow, including uracil. Next, 1 μL of the overnight culture, which was at an optical density (OD) as measured at 600 nM of >3.0, was diluted to an OD$_{600}$ of 0.01 in YPD and the culture incubated with shaking at 30° C. for an additional 24 hours. This process was repeated 3 more times for a total of 5 overnight incubations. This is the equivalent of greater than 100 generations of doublings (from the initial colony on the plate to the end of the last overnight incubation. Cells (five independent colonies that are ura⁻ and five that were wild type were then plated onto YPD plates at a cell density of 300 to 1,000 cells/plate and incubated for two days at 30° C. The cells from these plates were replica plated to the following plates and scored for growth following three days incubation at 30° C.; Synthetic Complete (SC) SC-ura (1.34% yeast nitrogen base and ammonium sulfate; 4×10⁻⁵% biotin; supplemented with all amino acids, NO supplemental uracil; 2% dextrose and 2% agar); SC+URA (same as SC-ura but supplement plate with 50 mg uracil/liter medium), and YPD plates. They were replica plated in the following order—SC -ura, SC complete, YPD. If the novel output trait that is resident within the yeast genome that was generated by expression of the mutant MMR (in this example the human homologue of PMS2, hPMS2-R2) is unstable, the uracil dependent cells should "revert" back a uracil independent phenotype. If the phenotype is stable, growth of the mutant cells under non-selective conditions should result in yeast cells that maintain their viability dependence on exogenous supplementation with uracil. As can be seen in the data presented in Table 2, the uracil dependent phenotype is stable when the yeast cells are grown under non-selective conditions, demonstrating that the MMR-generated phenotype derived from mutation in one of the uracil biosynthetic pathway genes is stable genetically.

| Strain | Seeded | -ura | +URA | YPD |
|---|---|---|---|---|
| Wt | 650 | 650 | 650 | 650 |
| Empty | 560 | 560 | 560 | 560 |
| pMOR$^{ye-1\#}$ | 730 | 0 | 730 | 730 |

These data demonstrate the utility of employing an inducible expression system and a dominant negative MMR gene in a eukaryotic system to generate genetically altered strains. The strain developed in this example, a yeast strain that now requires addition of uracil for growth, is potentially useful as a strain for recombinant manufacturing; by constructing an expression vector that harbors the wild type URA3 gene on either an integration plasmid or an extra-chromosomal vector it is now possible to transform and create novel cells expressing the a protein of interest. It is also possible to modify other resident genes in yeast cells and select for mutations in genes that that give other useful phenotypes, such as the ability to carry out a novel bio-transformation. Furthermore, it is possible to express a gene extra-chromosomally in a yeast cell that has altered MMR activity as described above and select for mutations in the extra-chromosomal gene. Therefore, in a similar manner to that described above the mutant yeast cell can be put under specific selective pressure and a novel protein with commercially important biochemical attributes selected. These examples are meant only as illustrations and are not meant to limit the scope of the present invention. Finally, as described above once a mutation has been introduced into the gene of interest the MMR activity is attenuated of completely abolished. The result is a yeast cell that harbors a stable mutation in the target gene(s) of interest.

Example 5

Enhanced Generation of MMR-Defective Yeast and Chemical Mutagens for the Generation of New Output Traits It has been previously documented that MMR deficiency yields to increased mutation frequency and increased resistance to toxic effects of chemical mutagens (CM) and their respective analogues such as but not limited to those as: ethidium bromide, EMS, MNNG, MNU, Tamoxifen, 8-Hydroxyguanine, as well as others listed but not limited to in publications by: Khromov-Borisov, N. N., et. al. Mutat. Res. 430:55-74, 1999; Ohe, T., et. al. (Mutat. Res. 429:189-199, 1999; Hour, T. C. et. al. Food Chem. Toxicol. 37:569-579, 1999; Hrelia, P., et. al. Chem. Biol. Interact. 118:99-111, 1999; Garganta, F., et. al. Environ. Mol. Mutagen. 33:75-85, 1999; Ukawa-Ishikawa S., et. al. Mutat. Res. 412:99-107, 1998; www.ehs.utah.edu/ohh/mutagens; Marcelino L A, Andre P C, Khrapko K, Coller H A, Griffith J, Thilly W G. Chemically induced mutations in mitochondrial DNA of human cells: mutational spectrum of N-methyl-N'-nitro-N-nitrosoguanidine. *Cancer Res* 1998 Jul. 1; 58(13):2857-62; Koi M, Umar A, Chauhan D P, Cheman S P, Carethers J M, Kunkel T A, Boland C R. Human chromosome 3 corrects mismatch repair deficiency and microsatellite instability and reduces N-methyl-N'-nitro-N-nitrosoguanidine tolerance in colon tumor cells with homozygous hMLH1 mutation. Can res 1994 54:4308-4312, 1994. Mismatch repair provokes chromosome aberrations in hamster cells treated with methylating agents or 6-thioguanine, but not with ethylating agents. To demonstrate the ability of CMs to increase the mutation frequency in MMR defective yeast cells, we would predict that exposure of yeast cells to CMs in the presence or absence of methanol (which induces the expression of the resident human homologue to PMS2, hPMS2-R2) will result in an augmentation of mutations within the yeast cell.

Yeast cells that express hPMS2-R2 (induced or un-induced) and empty vector control cells are grown as described in examples 2 and 3) and for 24 hours and diluted into MM medium as described above. Next, the cells in MM are incubated either with or without increasing amounts of ethyl methane sulfonate (EMS) from 0, 1, 10, 50, 100, and 200 μM. 10 μL aliquots of culture (diluted in 300 μl MM) and incubated for 30 minutes, 60 minutes, and 120 minutes followed by plating cells onto 5-FOA plates as described in example 3 above. Mutants are selected and scored as above. We would predict that there will be an increase in the frequency of ura⁻ mutants in the PMS2-R2 cultures that are induced with methanol as compared to the uninduced parental or wild type strain. In a further extension of this example, human PMS2-R2 harboring cells will be induced for 24 and 48 hours then mutagenized with EMS. This will allow the MMR gene to be fully active and expressed at high levels, thereby resulting in an increase in the number of ura⁻ mutants obtained. We would predict that there will be no change in the number of ura⁻ mutants obtained in the un-induced parental control or the wild type "empty vector" cells.

This example demonstrates the use of employing a regulated dominant negative MMR system plus chemical mutagens to produce enhanced numbers of genetically altered yeast strains that can be selected for new output traits. This method is useful for generating such organisms for commercial applications such as but not limited to recombinant manufacturing, biotransformation, and altered biochemicals with enhanced activities. It is also useful to obtain alterations of protein activity from ectopically expressed proteins harbored on extra-chromosomal expression vectors similar to those described in example 4 above.

Example 6

Alternative Methods to Inhibition of Yeast MMR Activity

The inhibition of MMR activity in a host organism can be achieved by introducing a dominant negative allele as shown in the examples above. This application also teaches us the use of using regulated systems to control MMR in yeast to generate genetic diversity and output traits for commercial applications. Additional methods to regulate the suppression of MMR activity of a host are by using genetic recombination to knock out alleles of a MMR gene within the cell of interest. This can be accomplished by use of homologous recombination that disrupts the endogenous MMR gene; 2) blocking MMR protein dimerization with other subunits (which is required for activity) by the introduction of polypeptides or antibodies into the host via transfection methods routinely used by those skilled in the art (e.g. electroporation); or 3) decreasing the expression of a MMR gene using anti-sense oligonucleotides.

MMR gene knockouts. We intend to generate disrupted targeting vectors of a particular MMR gene and introduce it into the genome of yeast using methods standard in the art. Yeast exhibiting hypermutability will be useful to produce genetically diverse offspring for commercial applications. Yeast will be confirmed to have lost the expression of the MMR gene using standard northern and biochemical techniques (as described in reference 31). MMR gene loci can be knocked out, strains selected for new output traits and MMR restored by introducing a wild type MMR gene to complement the KO locus. Other strategies include using KO vectors that can target a MMR gene locus, select for host output traits and then have the KO vector "spliced" from the genome after strain generation.

Blocking peptides. MMR subunits (MutS and MutL proteins) interact to form active MMR complexes. Peptides are able to specifically inhibit the binding of two proteins by competitive inhibition. Introduction into cells of peptides or antibodies to conserved domains of a particular MMR gene to disrupt activity is straightforward to those skilled in the art. Yeast will be verified for loss of expression of the MMR activity by standard northern and/or biochemical techniques (as described in Nicolaides N C, Littman S J, Modrich P, Kinzler K W, Vogelstein B 1998. A naturally occurring hPMS2 mutation can confer a dominant negative mutator phenotype. Mol Cell Biol 18: 1635-1641). Yeast exhibiting hypermutability will be useful to produce genetically diverse sibs for commercial applications.

Discussion

The results described above will lead to several conclusions. First, expression of dominant negative MMR proteins results in an increase in microsatellite instability and hypermutability in yeast. The hypermutability of the yeast cell is due to the inhibition of the resident, endogenous MMR biochemical activity in these hosts. This method provides a claim for use of MMR genes and their encoded products for the creation of hypermutable yeast to produce new output traits for commercial applications.

Examples of MMR Genes and Encoded Polypeptides

```
Yeast MLH1 cDNA (accession number U07187) (SEQ ID NO: 5)
   1 aaataggaat gtgatacctt ctattgcatg caaagatagt gtaggaggcg ctgctattgc
  61 caaagacttt tgagaccgct tgctgtttca ttatagttga ggagttctcg aagacgagaa
 121 attagcagtt ttcggtgttt agtaatcgcg ctagcatgct aggacaattt aactgcaaaa
 181 ttttgatacg atagtgatag taaatgaag gtaaaaataa catagaccta tcaataagca
 241 atgtctctca gaataaaagc acttgatgca tcagtggtta acaaaattgc tgcaggtgag
 301 atcataatat cccccgtaaa tgctctcaaa gaaatgatgg agaattccat cgatgcgaat
 361 gctacaatga ttgatattct agtcaaggaa ggaggaatta aggtacttca aataacagat
 421 aacggatctg gaattaataa agcagacctg ccaatcttat gtgagcgatt cacgacgtcc
 481 aaattacaaa aattcgaaga tttgagtcag attcaaacgt atggattccg aggagaagct
 541 ttagccagta tctcacatgt ggcaagagtc acagtaacga caaagttaa agaagacaga
 601 tgtgcatgga gagtttcata tgcagaaggt aagatgttgg aaagcccaa acctgttgct
 661 ggaaaagacg gtaccacgat cctagttgaa gaccttttt tcaatattcc ttctagatta
 721 agggccttga ggtcccataa tgatgaatac tctaaaatat tagatgttgt cgggcgatac
 781 gccattcatt ccaaggacat tggcttttct tgtaaaaagt tcggagactc taattattct
 841 ttatcagtta aaccttcata tacagtccag gataggatta ggactgtgtt caataaatct
 901 gtggcttcga atttaattac ttttcatatc agcaaagtag aagatttaaa cctggaaagc
 961 gttgatggaa aggtgtgtaa tttgaatttc atatccaaaa agtccatttc attaattttt
1021 ttcattaata atagactagt gacatgtgat cttctaagaa gagctttgaa cagcgtttac
```

-continued

```
1081  tccaattatc tgccaagggg cttcagacct tttatttatt tgggaattgt tatagatccg
1141  gcggctgttg atgttaacgt tcacccgaca agagagagg ttcgtttcct gagccaagat
1201  gagatcatag agaaaatcgc caatcaattg cacgccgaat tatctgccat tgatacttca
1261  cgtactttca aggcttcttc aatttcaaca aacaagccag agtcattgat accatttaat
1321  gacaccatag aaagtgatag aataggaag agtctccgac aagcccaagt ggtagagaat
1381  tcatatacga cagccaatag tcaactaagg aaagcgaaaa gacaagagaa taaactagtc
1441  agaatagatg cttcacaagc taaaattacg tcatttttat cctcaagtca acagttcaac
1501  tttgaaggat cgtctacaaa gcgacaactg agtgaaccca aggtaacaaa tgtaagccac
1561  tcccaagagg cagaaaagct gacactaaat gaaagcgaac aaccgcgtga tgccaataca
1621  atcaatgata atgacttgaa ggatcaacct aagaagaaac aaaagttggg ggattataaa
1681  gttccaagca ttgccgatga cgaaaagaat gcactcccga tttcaaaaga cgggtatatt
1741  agagtaccta aggagcgagt taatgttaat cttacgagta tcaagaaatt gcgtgaaaaa
1801  gtagatgatt cgatacatcg agaactaaca gacattttg caaatttgaa ttacgttggg
1861  gttgtagatg aggaaagaag attagccgct attcagcatg acttaaagct tttttttaata
1921  gattacggat ctgtgtgcta tgagctattc tatcagattg gtttgacaga cttcgcaaac
1981  tttggtaaga taaacctaca gagtacaaat gtgtcagatg atatagtttt gtataatctc
2041  ctatcagaat ttgacgagtt aaatgacgat gcttccaaag aaaaaataat tagtaaaata
2101  tgggacatga gcagtatgct aaatgagtac tattccatag aattggtgaa tgatggtcta
2161  gataatgact taaagtctgt gaagctaaaa tctctaccac tacttttaaa aggctacatt
2221  ccatctctgg tcaagttacc attttttata tatcgcctgg gtaaagaagt tgattgggag
2281  gatgaacaag agtgtctaga tggtatttta agagagattg cattactcta tatacctgat
2341  atggttccga aagtcgatac actcgatgca tcgttgtcag aagacgaaaa agcccagttt
2401  ataaatagaa aggaacacat atcctcatta ctagaacacg ttctcttccc ttgtatcaaa
2461  cgaaggttcc tggcccctag acacattctc aaggatgtcg tggaaatagc caaccttcca
2521  gatctataca aagttttga gaggtgttaa ctttaaaacg ttttggctgt aataccaaag
2581  tttttgttta tttcctgagt gtgattgtgt ttcatttgaa agtgtatgcc cttttccttta
2641  acgattcatc cgcgagattt caaaggatat gaaatatggt tgcagttagg aaagtatgtc
2701  agaaatgtat attcggattg aaactcttct aatagttctg aagtcacttg gttccgtatt
2761  gttttcgtcc tcttcctcaa gcaacgattc ttgtctaagc ttattcaacg gtaccaaaga
2821  cccgagtcct tttatgagag aaaacatttc atcattttc aactcaatta tcttaatatc
2881  attttgtagt attttgaaaa caggatggta aaacgaatca cctgaatcta gaagctgtac
2941  cttgtcccat aaaagttta atttactgag cctttcggtc aagtaaacta gtttatctag
3001  ttttgaaccg aatattgtgg gcagatttgc agtaagttca gttagatcta ctaaaagttg
3061  tttgacagca gccgattcca caaaaatttg gtaaaaggag atgaaagaga cctcgcgcgt
3121  aatggtttgc atcaccatcg gatgtctgtt gaaaaactca cttttgcat ggaagttatt
3181  aacaataaga ctaatgatta ccttagaata atgtataa
```

Yeast MLH1 protein (accession number U07187) (SEQ ID NO: 15)
MSLRIKALDASVVNKIAAGEIIISPVNALKEMMENSIDANATMI

DILVKEGGIKVLQITDNGSGINKADLPILCERFTTSKLQKFEDLSQIQTYGFRGEALA

SISHVARVTVTTKVKEDRCAWRVSYAEGKMLESPKPVAGKDGTTILVEDLFFNIPSRL

-continued

```
RALRSHNDEYSKILDVVGRYAIHSKDIGFSCKKFGDSNYSLSVKPSYTVQDRIRTVFN

KSVASNLITFHISKVEDLNLESVDGKVCNLNFISKKSISLIFFINNRLVTCDLLRRAL

NSVYSNYLPKGFRPFIYLGIVIDPAAVDVNVHPTKREVRFLSQDEIIEKIANQLHAEL

SAIDTSRTFKASSISTNKPESLIPFNDTIESDRNRKSLRQAQVVENSYTTANSQLRKA

KRQENKLVRIDASQAKITSFLSSSQQFNFEGSSTKRQLSEPKVTNVSHSQEAEKLTLN

ESEQPRDANTINDNDLKDQPKKKQKLGDYKVPSIADDEKNALPISKDGYIRVPKERVN

VNLTSIKKLREKVDDSIHRELTDIFANLNYVGVVDEERRLAAIQHDLKLFLIDYGSVC

YELFYQIGLTDFANFGKINLQSTNVSDDIVLYNLLSEFDELNDDASKEKIISKIWDMS

SMLNEYYSIELVNDGLDNDLKSVKLKSLPLLLKGYIPSLVKLPFFIYRLGKEVDWEDE

QECLDGILREIALLYIPDMVPKVDTLDASLSEDEKAQFINRKEHISSLLEHVLFPCIK

RRFLAPRHILKDVVEIANLPDLYKVFERC
```

```
Mouse PMS2 protein (SEQ ID NO: 16)
MEQTEGVSTE CAKAIKPIDG KSVHQICSGQ VILSLSTAVK ELIENSVDAG ATTIDLRLKD      60

YGVDLIEVSD NGCGVEEENF EGLALKHHTS KIQEFADLTQ VETFGFRGEA LSSLCALSDV     120

TISTCHGSAS VGTRLVFDHN GKITQKTPYP RPKGTTVSVQ HLFYTLPVRY KEFQRNIKKE     180

YSKMVQVLQA YCIISAGVRV SCTNQLGQGK RHAVVCTSGT SGMKENIGSV FGQKQLQSLI     240

PFVQLPPSDA VCEEYGLSTS GRHKTFSTFR ASFHSARTAP GGVQQTGSFS SSIRGPVTQQ     300

RSLSLSMRFY HMYNRHQYPF VVLNVSVDSE CVDINVTPDK RQILLQEEKL LLAVLKTSLI     360

GMFDSDANKL NVNQQPLLDV EGNLVKLHTA ELEKPVPGKQ DNSPSLKSTA DEKRVASISR     420

LREAFSLHPT KEIKSRGPET AELTRSFPSE KRGVLSSYPS DVISYRGLRG SQDKLVSPTD     480

SPGDCMDREK TEKDSGLSST SAGSEEEFST PEVASSFSSD YNVSSLEDRP SQETINCGDL     540

DCRPPGTGQS LKPEDHGYQC KALPLARLSP TNAKRFKTEE RPSNVNISQR LPGPQSTSAA     600

EVDVAIKMNK RIVLLEFSLS SLAKRMKQLQ HLKAQNKHEL SYRKFRAKIC PGENQAAEDE     660

LRKEISKSMF AEMEILGQFN LGFIVTKLKE DLFLVDQHAA DEKYNFEMLQ QHTVLQAQRL     720

ITPQTLNLTA VNEAVLIENL EIFRKNGFDF VIDEDAPVTE RAKLISLPTS KNWTFGPQDI     780

DELIFMLSDS PGVMCRPSRV RQMFASRACR KSVMIGTALN ASEMKKLITH MGEMDHPWNC     840

PHGRPTMRHV ANLDVISQN                                                 859
```

```
Mouse PMS2 cDNA (SEQ ID NO: 6)
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg gcaggtgat actcagttta agcaccgctg     300
tgaaggagtt gatagaaaat agtgtagatg ctggtgctac tactattgat ctaaggctta     360
aagactatgg ggtggacctc attgaagttt cagacaatgg atgtggggta gaagaagaaa     420
actttgaagg tctagctctg aaacatcaca catctaagat tcaagagttt gccgacctca     480
cgcaggttga actttcggc tttcgggggg aagctctgag ctctctgtgt gcactaagtg     540
atgtcactat atctacctgc cacgggtctg caagcgttgg gactcgactg gtgtttgacc     600
ataatgggaa aatcacccag aaaactccct accccgacc taaggaacc acagtcagtg     660 tgcagcactt attttataca ctacccgtgc gttacaaaga gttcagagg aacattaaaa     720 aggagtattc caaaatggtg caggtcttac aggcgtactg tatcatctca gcaggcgtcc     780
```

```
                                         -continued
gtgtaagctg cactaatcag ctcggacagg ggaagcggca cgctgtggtg tgcacaagcg    840
gcacgtctgg catgaaggaa aatatcgggt ctgtgtttgg ccagaagcag ttgcaaagcc    900
tcattccttt tgttcagctg ccccctagtg acgctgtgtg tgaagagtac ggcctgagca    960
cttcaggacg ccacaaaacc ttttctacgt ttcgggcttc atttcacagt gcacgcacgg   1020
cgccgggagg agtgcaacag acaggcagtt tttcttcatc aatcagaggc cctgtgaccc   1080
agcaaaggtc tctaagcttg tcaatgaggt tttatcacat gtataaccgg catcagtacc   1140
catttgtcgt ccttaacgtt tccgttgact cagaatgtgt ggatattaat gtaactccag   1200
ataaaaggca aattctacta caagaagaga agctattgct ggccgtttta aagacctcct   1260
tgataggaat gtttgacagt gatgcaaaca agcttaatgt caaccagcag ccactgctag   1320
atgttgaagg taacttagta aagctgcata ctgcagaact agaaaagcct gtgccaggaa   1380
agcaagataa ctctccttca ctgaagagca cagcagacga gaaagggta gcatccatct   1440 ccaggctgag agaggccttt tctcttcatc ctactaaaga gatcaagtct aggggtccag   1500
agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaaagactca gggctcagca   1680
gcacctcagc tggctctgag gaagagttca gcacccagaa agtggccagt agctttagca   1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt cacccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt acagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga agaggacct cttcctggtg gaccagcatg    2280
ctgcggatga aagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatggctttg actttgtcat tgatgaggat gctccagtca   2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacggcgc   2640
tcaatgcgag cgagatgaag aagctcatca cccacatggg tgagatggac caccctgga   2700 actgcccca cggcaggcca accatgaggc acgttgccaa tctggatgtc atctctcaga   2760
actgacacac cccttgtagc atagagttta ttacagattg ttcggtttgc aaagagaagg   2820
ttttaagtaa tctgattatc gttgtacaaa aattagcatg ctgctttaat gtactggatc   2880 cattttaaaag cagtgttaag gcaggcatga tggagtgttc ctctagctca gctacttggg   2940
tgatccggtg ggagctcatg tgagcccagg actttgagac cactccgagc cacattcatg   3000
agactcaatt caaggacaaa aaaaaaaaga tattttgaa gccttttaaa aaaaaa        3056

Human PMS2 protein (SEQ ID NO: 7)
MKQLPAATVR LLSSSQIITS VVSVVKELIE NSLDAGATSV DVKLENYGFD KIEVRDNGEG     60

IKAVDAPVMA MKYYTSKINS HEDLENLTTY GFRGEALGSI CCIAEVLITT RTAADNFSTQ    120
```

```
YVLDGSGHIL SQKPSHLGQG TTVTALRLFK NLPVRKQFYS TAKKCKDEIK KIQDLLMSFG    180

ILKPDLRIVF VHNKAVIWQK SRVSDHKMAL MSVLGTAVMN NMESFQYHSE ESQIYLSGFL    240

PKCDADHSFT SLSTPERSFI FINSRPVHQK DILKLIRHHY NLKCLKESTR LYPVFFLKID    300

VPTADVDVNL TPDKSQVLLQ NKESVLIALE NLMTTCYGPL PSTNSYENNK TDVSAADIVL    360

SKTAETDVLF NKVESSGKNY SNVDTSVIPF QNDMHNDESG KNTDDCLNHQ ISIGDFGYGH    420

CSSEISNIDK NTKNAFQDIS MSNVSWENSQ TEYSKTCFIS SVKHTQSENG NKDHIDESGE    480

NEEEAGLENS SEISADEWSR GNILKNSVGE NIEPVKILVP EKSLPCKVSN NNYPIPEQMN    540

LNEDSCNKKS NVIDNKSGKV TAYDLLSNRV IKKPMSASAL FVQDHRPQFL IENPKTSLED    600

ATLQIEELWK TLSEEEKLKY EEKATKDLER YNSQMKEAIE QESQMSLKDG RKKIKPTSAW    660

NLAQKHKLKT SLSNQPKLDE LLQSQIEKRR SQNIKMVQIP FSMKNLKINF KKQNKVDLEE    720

KDEPCLIHNL RFPDAWLMTS KTEVMLLNPY RVEEALLFKR LLENHKLPAE PLEKPIMLTE    780

SLFNGSHYLD VLYKMTADDQ RYSGSTYLSD PRLTANGFKI KLIPGVSITE NYLEIEGMAN    840

CLPFYGVADL KEILNAILNR NAKEVYECRP RKVISYLEGE AVRLSRQLPM YLSKEDIQDI    900

IYRMKHQFGN EIKECVHGRP FFHHLTYLPE TT                                 932

Human PMS2 cDNA (SEQ ID NO: 17)
cgaggcggat cgggtgttgc atccatggag cgagctgaga gctcgagtac agaacctgct      60
aaggccatca aacctattga tcggaagtca gtccatcaga tttgctctgg caggtggta     120 ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt     300 caagagtttg ccgacctaac tcaggttgaa acttttggct tcgggggga agctctgagc    360 tcactttgtg cactgagcga tgtcaccatt tctacctgcc acgcatcggc gaaggttgga    420
actcgactga tgtttgatca aatgggaaa attatccaga aaaccccta ccccgcccc      480 agagggacca cagtcagcgt gcagcagtta ttttccacac tacctgtgcg ccataaggaa    540
tttcaaagga atattaagaa ggagtatgcc aaaatggtcc aggtcttaca tgcatactgt    600
atcatttcag caggcatccg tgtaagttgc accaatcagc ttggacaagg aaaacgacag    660
cctgtggtat gcacaggtgg aagcccccagc ataaaggaaa atatcggctc tgtgtttggg    720
cagaagcagt tgcaaagcct cattcctttt gttcagctgc cccctagtga ctccgtgtgt    780
gaagagtacg gtttgagctg ttcggatgct ctgcataatc tttttacat ctcaggtttc     840 atttcacaat gcacgcatgg agttggaagg agttcaacag acagacagtt tttcttatc     900 aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaggcaa atttttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca agaaggagcc ctctaggaca gaaaaggggt   1380
atgctgtctt ctagcacttc aggtgccatc tctgacaaag cgtcctgag acctcagaaa   1440 gaggcagtga gttccagtca cggacccagt gaccctacgg acagagcgga ggtggagaag   1500
```

```
gactcggggc acggcagcac ttccgtggat tctgaggggt tcagcatccc agacacgggc    1560
agtcactgca gcagcgagta tgcggccagc tccccagggg acaggggctc gcaggaacat    1620
gtggactctc aggagaaagc gcctgaaact gacgactctt tttcagatgt ggactgccat    1680
tcaaaccagg aagataccgg atgtaaattt cgagttttgc ctcagccaac taatctcgca    1740
accccaaaca caaagcgttt taaaaaagaa gaaattcttt ccagttctga catttgtcaa    1800
aagttagtaa atactcagga catgtcagcc tctcaggttg atgtagctgt gaaaattaat    1860
aagaaagttg tgccctggaa cttttctatg agttctttag ctaaacgaat aaagcagtta    1920
catcatgaag cacagcaaag tgaaggggaa cagaattaca ggaagtttag ggcaaagatt    1980
tgtcctggag aaaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca cccctggaac tgtccccatg aaggccaac  catgagacac    2580 atcgcccacc tgggtgtcat ttctcagaac tgaccgtagt cactgtatgg aataattggt    2640
tttatcgcag attttatgt tttgaaagac agagtcttca ctaacctttt ttgttttaaa    2700
atgaaacctg ctactaaaa aaaatacaca tcacacccat ttaaaagtga tcttgagaac    2760
cttttcaaac c                                                         2771
```

Human PMS1 protein (SEQ ID NO: 18)

```
MKQLPAATVR LLSSSQIITS VVSVVKELIE NSLDAGATSV DVKLENYGFD KIEVRDNGEG     60

IKAVDAPVMA MKYYTSKINS HEDLENLTTY GFRGEALGST CCIAEVLTTT RTAADNFSTQ    120

YVLDGSGHIL SQKPSHLGQG TTVTALRLFK NLPVRKQFYS TAKKCKDEIK KIQDLLMSFG    180

ILKPDLRIVF VHNKAVIWQK SRVSDHKMAL MSVLGTAVMN NMESFQYHSE ESQIYLSGFL    240

PKCDADHSFT SLSTPERSFI FINSRPVHQK DILKLIRHHY NLKCLKESTR LYPVFFLKID    300

VPTADVDVNL TPDKSQVLLQ NKESVLIALE NLMTTCYGPL PSTNSYENNK TDVSAADIVL    360

SKTAETDVLF NKVESSGKNY SNVDTSVIPF QNDMHNDESG KNTDDCLNHQ ISIGDFGYGH    420

CSSEISNIDK NTKNAFQDIS MSNVSWENSQ TEYSKTCFIS SVKHTQSENG NKDHIDESGE    480

NEEEAGLENS SEISADEWSR GNILKNSVGE NIEPVKILVP EKSLPCKVSN NNYPIPEQMN    540

LNEDSCNKKS NVIDNKSGKV TAYDLLSNRV IKKPMSASAL FVQDHRPQFL IENPKTSLED    600

ATLQIEELWK TLSEEEKLKY EEKATKDLER YNSQMKEAIE QESQMSLKDG RKKIKPTSAW    660

NLAQKHKLKT SLSNQPKLDE LLQSQIEKRR SQNIKMVQIP FSMKNLKINF KKQNKVDLEE    720

KDEPCLIHNL RFPDAWLMTS KTEVMLLNPY RVEEALLFKR LLENHKLPAE PLEKPIMLTE    780

SLFNGSHYLD VLYKMTADDQ RYSGSTYLSD PRLTANGFKI KLIPGVSITE NYLEIEGMAN    840

CLPFYGVADL KEILNAILNR NAKEVYECRP RKVISYLEGE AVRLSRQLPM YLSKEDIQDI    900

IYRMKHQFGN EIKECVHGRP FFHHLTYLPE TT                                  932
```

Human PMS1 cDNA (SEQ ID NO: 8)

```
ggcacgagtg gctgcttgcg gctagtggat ggtaattgcc tgcctcgcgc tagcagcaag     60
```

-continued

```
ctgctctgtt aaaagcgaaa atgaaacaat tgcctgcggc aacagttcga ctcctttcaa      120
gttctcagat catcacttcg gtggtcagtg ttgtaaaaga gcttattgaa aactccttgg      180
atgctggtgc cacaagcgta gatgttaaac tggagaacta tggatttgat aaaattgagg      240
tgcgagataa cggggagggt atcaaggctg ttgatgcacc tgtaatggca atgaagtact      300
acacctcaaa aataaatagt catgaagatc ttgaaaattt gacaacttac ggttttcgtg      360
gagaagcctt ggggtcaatt tgttgtatag ctgaggtttt aattacaaca agaacggctg      420
ctgataattt tagcacccag tatgttttag atggcagtgg ccacatactt tctcagaaac      480
cttcacatct tggtcaaggt acaactgtaa ctgctttaag attatttaag aatctacctg      540
taagaaagca gttttactca actgcaaaaa aatgtaaaga tgaaataaaa aagatccaag      600
atctcctcat gagctttggt atccttaaac ctgacttaag gattgtcttt gtacataaca      660
aggcagttat ttggcagaaa agcagagtat cagatcacaa gatggctctc atgtcagttc      720
tggggactgc tgttatgaac aatatggaat cctttcagta ccactctgaa gaatctcaga      780
tttatctcag tggatttctt ccaaagtgtg atgcagacca ctctttcact agtctttcaa      840
caccagaaag aagtttcatc ttcataaaca gtcgaccagt acatcaaaaa gatatcttaa      900
agttaatccg acatcattac aatctgaaat gcctaaagga atctactcgt ttgtatcctg      960
ttttctttct gaaaatcgat gttcctacag ctgatgttga tgtaaattta acaccagata     1020
aaagccaagt attattacaa ataaggaat ctgtttttaat tgctcttgaa atctgatga      1080
```

```
cgacttgtta tggaccatta cctagtacaa attcttatga aaataataaa acagatgttt      1140
ccgcagctga catcgttctt agtaaaacag cagaaacaga tgtgcttttt aataaagtgg      1200
aatcatctgg aaagaattat tcaaatgttg atacttcagt cattccattc caaaatgata      1260
tgcataatga tgaatctgga aaaaacactg atgattgttt aaatcaccag ataagtattg      1320
gtgactttgg ttatggtcat tgtagtagtg aaatttctaa cattgataaa aacactaaga      1380
atgcatttca ggacatttca atgagtaatg tatcatggga gaactctcag acggaatata      1440
gtaaaacttg ttttataagt tccgttaagc acacccagtc agaaaatggc aataaagacc      1500
atatagatga gagtggggaa aatgaggaag aagcaggtct tgaaaactct tcggaaattt      1560
ctgcagatga gtggagcagg ggaaatatac ttaaaaattc agtgggagag aatattgaac      1620
ctgtgaaaat tttagtgcct gaaaaaagtt taccatgtaa agtaagtaat aataattatc      1680
caatccctga acaaatgaat cttaatgaag attcatgtaa caaaaaatca aatgtaatag      1740
ataataaatc tggaaaagtt acagcttatg atttacttag caatcgagta atcaagaaac      1800
ccatgtcagc aagtgctctt tttgttcaag atcatcgtcc tcagtttctc atagaaaatc      1860
ctaagactag tttagaggat gcaacactac aaattgaaga actgtggaag acattgagtg      1920
aagaggaaaa actgaaatat gaagagaagg ctactaaaga cttggaacga tacaatagtc      1980
aaatgaagag agccattgaa caggagtcac aaatgtcact aaaagatggc agaaaaaaga      2040 taaacccac cagcgcatgg aatttggccc agaagcacaa gttaaaaacc tcattatcta      2100
atcaaccaaa acttgatgaa ctccttcagt cccaaattga aaaagaagg agtcaaaata      2160 ttaaaatggt acagatcccc ttttctatga aaaacttaaa aataaatttt aagaaacaaa      2220
acaaagttga cttagaagag aaggatgaac cttgcttgat ccacaatctc aggtttcctg      2280
atgcatggct aatgacatcc aaaacagagg taatgttatt aaatccatat agagtagaag      2340
aagccctgct atttaaaaga cttcttgaga atcataaact tcctgcagag ccactggaaa      2400
agccaattat gttaacagag agtctttttta atggatctca tatttagac gttttatata     2460
```

-continued

```
aaatgacagc agatgaccaa agatacagtg gatcaactta cctgtctgat cctcgtctta   2520
cagcgaatgg tttcaagata aaattgatac caggagtttc aattactgaa aattacttgg   2580
aaatagaagg aatggctaat tgtctcccat tctatggagt agcagattta aagaaaattc   2640
ttaatgctat attaaacaga aatgcaaagg aagtttatga atgtagacct cgcaaagtga   2700
taagttattt agagggagaa gcagtgcgtc tatccagaca attacccatg tacttatcaa   2760
aagaggacat ccaagacatt atctacgaaa tgaagcacca gtttggaaat gaaattaaag   2820
agtgtgttca tggtcgccca tttttcatc atttaaccta tcttccagaa actacatgat    2880
taaatatgtt taagaagatt agttaccatt gaaattggtt ctgtcataaa acagcatgag   2940
tctggtttta aattatcttt gtattatgtg tcacatggtt attttttaaa tgaggattca   3000
ctgacttgtt tttatattga aaaagttcc acgtattgta gaaaacgtaa ataaactaat    3060
aac                                                                 3063
```

Human MSH2 protein (SEQ ID NO: 19)
```
MAVQPKETLQ LESAAEVGFV RFFQGMPEKP TTTVRLFDRG DFYTAHGEDA LLAAREVFKT    60
QGVIKYMGPA GAKNLQSVVL SKMNFESFVK DLLLVRQYRV EVYKNRAGNK ASKENDWYLA   120
YKASPGNLSQ FEDILFGNND MSASIGVVGV KMSAVDGQRQ VGVGYVDSIQ RKLGLCEFPD   180
NDQFSNLEAL LIQIGPKECV LPGGETAGDM GKLRQIIQRG GILITERKKA DFSTKDIYQD   240
LNRLLKGKKG EQMNSAVLPE MENQVAVSSL SAVIKFLELL SDDSNFGQFE LTTFDFSQYM   300
KLDIAAVEAL NLFQGSVEDT TGSQSLAALL NKCKTPQGQR LVNQWIKQPL MDKNRIEERL   360
NLVEAFVEDA ELRQTLQEDL LRRFPDLNRL AKKFQRQAAN LQDCYRLYQG INQLPNVIQA   420
LEKHEGKHQK LLLAVFVTPL TDLRSDFSKF QEMIETTLDM DQVENHEFLV KPSFDPNLSE   480
LREIMNDLEK KMQSTLISAA RDLGLDPGKQ IKLDSSAQFG YYFRVTCKEE KVLRNNKNFS   540
TVDIQKNGVK FTNSKLTSLN EEYTKNKTEY EEAQDAIVKE IVNISSGYVE PMQTLNDVLA   600
QLDAVVSFAH VSNGAPVPYV RPAILEKGQG RIILKASRHA CVEVQDEIAF IPNDVYFEKD   660
KQMFHIITGP NMGGKSTYIR QTGVIVLMAQ IGCFVPCESA EVSIVDCILA RVGAGDSQLK   720
GVSTFMAEML ETASILRSAT KDSLIIIDEL GRGTSTYDGF GLAWAISEYI ATKIGAFCMF   780
ATHFHELTAL ANQIPTVNNL HVTALTTEET LTMLYQVKKG VCDQSFGIHV AELANFPKHV   840
IECAKQKALE LEEFQYIGES QGYDIMEPAA KKCYLEREQG EKIIQEFLSK VKQMPFTEMS   900
EENITIKLKQ LKAEVIAKNN SFVNEIISRI KVTT                               934
```

Human MSH2 cDNA (SEQ ID NO: 9)
```
ggcgggaaac agcttagtgg gtgtggggtc gcgcattttc ttcaaccagg aggtgaggag    60
gtttcgacat ggcggtgcag ccgaaggaga cgctgcagtt ggagagcgcg gccgaggtcg   120
gcttcgtgcg cttctttcag ggcatgccgg agaagccgac caccacagtg cgccttttcg   180
accgggcga cttctatacg gcgcacggcg aggacgcgct gctggccgcc cgggaggtgt    240
tcaagaccca ggggggtgatc aagtacatgg ggccggcagg agcaaagaat ctgcagagtg   300
ttgtgcttag taaaatgaat tttgaatctt ttgtaaaaga tcttcttctg gttcgtcagt   360
atagagttga agtttataag aatagagctg gaaataaggc atccaaggag aatgattggt   420
atttggcata taaggcttct cctggcaatc tctctcagtt tgaagacatt ctctttggta   480
acaatgatat gtcagcttcc attggtgttg tgggtgttaa aatgtccgca gttgatggcc   540
agagacaggt tggagttggg tatgtggatt ccatacagag gaaactagga ctgtgtgaat   600
tccctgataa tgatcagttc tccaatcttg aggctctcct catccagatt ggaccaaagg   660
aatgtgtttt acccggagga gagactgctg gagacatggg gaaactgaga cagataattc   720
```

-continued

```
aaagaggagg aattctgatc acagaaagaa aaaaagctga cttttccaca aaagacattt    780
atcaggacct caaccggttg ttgaaaggca aaaaggagaa gcagatgaat agtgctgtat    840
tgccagaaat ggagaatcag gttgcagttt catcactgtc tgcggtaatc aagttttag    900 aactcttatc agatgattcc aactttggac agtttgaact gactactttt gacttcagcc    960
agtatatgaa attggatatt gcagcagtca gagcccttaa cctttttcag ggttctgttg   1020
aagataccac tggctctcag tctctggctg ccttgctgaa taagtgtaaa accccctcaag  1080 gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gttttgtga   1380 ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact tggaaaagaa gatgcagtca acattaataa   1560
gtgcagccag agatcttggc ttggaccctg gcaaacagat taaactggat tccagtgcac   1620
agtttggata ttactttcgt gtaacctgta aggaagaaaa agtccttcgt aacaataaaa   1680
actttagtac tgtagatatc cagaagaatg gtgttaaatt taccaacagc aaattgactt   1740 cttttaaatga gagtatacc aaaaataaaa cagaatatga agaagcccag gatgccattg   1800
ttaaagaaat tgtcaatatt tcttcaggct atgtagaacc aatgcagaca ctcaatgatg   1860
tgttagctca gctagatgct gttgtcagct ttgctcacgt gtcaaatgga gcacctgttc   1920
catatgtacg accagccatt ttggagaaag gacaaggaag aattatatta aaagcatcca   1980
ggcatgcttg tgttgaagtt caagatgaaa ttgcatttat tcctaatgac gtatactttg   2040
aaaaagataa acagatgttc cacatcatta ctggccccaa tatgggaggt aaatcaacat   2100
atattcgaca aactggggtg atagtactca tggcccaaat tgggtgtttt gtgccatgtg   2160
agtcagcaga agtgtccatt gtggactgca tcttagcccg agtaggggct ggtgacagtc   2220
aattgaaagg agtctccacg ttcatggctg aaatgttgga aactgcttct atcctcaggt   2280
ctgcaaccaa agattcatta ataatcatag atgaattggg aagaggaact tctacctacg   2340
atggatttgg gttagcatgg gctatatcag aatacattgc aacaaagatt ggtgcttttt   2400
gcatgtttgc aacccatttt catgaactta ctgccttggc caatcagata ccaactgtta   2460
ataatctaca tgtcacagca ctcaccactg aagagacctt aactatgctt tatcaggtga   2520
agaaaggtgt ctgtgatcaa agttttggga ttcatgttgc agagcttgct aatttcccta   2580
agcatgtaat agagtgtgct aaacagaaag ccctggaact tgaggagttt cagtatattg   2640
gagaatcgca aggatatgat atcatggaac cagcagcaaa gaagtgctat ctggaaagag   2700
agcaaggtga aaaattatt caggagttcc tgtccaaggt gaaacaaatg cccttactg    2760 aaatgtcaga agaaaacatc acaataaagt taaacagct aaaagctgaa gtaatagcaa   2820
agaataatag ctttgtaaat gaaatcattt cacgaataaa agttactacg tgaaaaatcc   2880
cagtaatgga atgaaggtaa tattgataag ctattgtctg taatagtttt atattgtttt   2940
atattaaccc ttttccata gtgttaactg tcagtgccca tgggctatca acttaataag   3000
atatttagta atattttact ttgaggacat tttcaaagat ttttattttg aaaaatgaga   3060
gctgtaactg aggactgttt gcaattgaca taggcaataa taagtgatgt gctgaatttt   3120
```

-continued ataaataaaa tcatgtagtt tgtgg                                             3145

Human MLH1 protein (SEQ ID NO: 20)
MSFVAGVIRR LDETVVNRIA AGEVIQRPAN AIKEMIENCL DAKSTSIQVI VKEGGLKLIQ         60
IQDNGTGIRK EDLDIVCERF TTSKLQSFED LASISTYGFR GEALASISHV AHVTITIKTA        120
DGKCAYRASY SDGKLKAPPK PCAGNQGTQI TVEDLFYNIA TRRKALKNPS EEYGKILEVV        180
GRYSVHNAGI SFSVKKQGET VADVRTLPNA STVDNIRSIF GNAVSRELIE IGCEDKTLAF        240
KMNGYISNAN YSVKKCIFLL FINHRLVEST SLRKAIETVY AAYLPKNTHP FLYLSLEISP        300
QNVDVNVHPT KHEVHFLHEE SILERVQQHI ESKLLGSNSS RMYFTQTLLP GLAGPSGEMV        360
KSTTSLTSSS TSGSSDKVYA HQMVRTDSRE QKLDAFLQPL SKPLSSQPQA IVTEDKTDIS        420
SGRARQQDEE MLELPAPAEV AAKNQSLEGD TTKGTSEMSE KRGPTSSNPR KRHREDSDVE        480
MVEDDSRKEM TAACTPRRRI INLTSVLSLQ EEINEQGHEV LREMLHNHSF VGCVNPQWAL        540
AQHQTKLYLL NTTKLSEELF YQILIYDFAN FGVLRLSEPA PLFDLAMLAL DSPESGWTEE        600
DGPKEGLAEY IVEFLKKKAE MLADYFSLEI DEEGNLIGLP LLIDNYVPPL EGLPIFILRL        660
ATEVNWDEEK ECFESLSKEC AMFYSIRKQY ISEESTLSGQ QSEVPGSIPN SWKWTVEHIV        720
YKALRSHILP PKHFTEDGNI LQLANLPDLY KVFERC                                 756

Human MLH1 cDNA (SEQ ID NO: 10)
cttggctctt ctggcgccaa aatgtcgttc gtggcagggg ttattcggcg gctggacgag         60
acagtggtga accgcatcgc ggcggggaa gttatccagc ggccagctaa tgctatcaaa        120
gagatgattg agaactgttt agatgcaaaa tccacaagta ttcaagtgat tgttaaagag        180
ggaggcctga agttgattca gatccaagac aatggcaccg ggatcaggaa agaagatctg        240
gatattgtat gtgaaaggtt cactactagt aaactgcagt cctttgagga tttagccagt        300
atttctacct atggctttcg aggtgaggct ttggccagca taagccatgt ggctcatgtt        360
actattacaa cgaaaacagc tgatggaaag tgtgcataca gagcaagtta ctcagatgga        420
aaactgaaag cccctcctaa accatgtgct ggcaatcaag ggacccagat cacggtggag        480
gaccttttt acaacatagc cacgaggaga aaagctttaa aaatccaag tgaagaatat        540
gggaaaattt ggaagttgt tggcaggtat tcagtacaca atgcaggcat tagtttctca        600
gttaaaaaac aaggagagac agtagctgat gttaggacac tacccaatgc ctcaaccgtg        660
gacaatattc gctccatctt tggaaatgct gttagtcgag aactgataga aattggatgt        720
gaggataaaa ccctagcctt caaaatgaat ggttacatat ccaatgcaaa ctactcagtg        780
aagaagtgca tcttcttact cttcatcaac atcgtctgg tagaatcaac ttccttgaga        840
aaagccatag aaacagtgta tgcagcctat ttgcccaaaa acacacaccc attcctgtac        900
ctcagtttag aaatcagtcc ccagaatgtg atgttaatg tgcaccccac aaagcatgaa        960
gttcacttcc tgcacgagga gagcatcctg agcgggtgc agcagcacat cgagagcaag       1020
ctcctgggct ccaattcctc caggatgtac ttcacccaga ctttgctacc aggacttgct       1080
gcccctctg gggagatggt taaatccaca acaagtctga cctcgtcttc tacttctgga       1140
agtagtgata aggtctatgc ccaccagatg gttcgtacag attcccggga acagaagctt       1200
gatgcatttc tgcagcctct gagcaaaccc ctgtccagtc agccccaggc cattgtcaca       1260
gaggataaga cagatatttc tagtggcagg ctaggcagc aagatgagga gatgcttgaa       1320
ctcccagccc ctgctgaagt ggctgccaaa atcagagct tggagggga tacaacaaag       1380
gggacttcag aaatgtcaga agagagga cctacttcca gcaacccag aaagagacat       1440
cgggaagatt ctgatgtgga aatggtggaa gatgattccc gaaaggaaat gactgcagct       1500

```
                                        -continued
tgtacccccc ggagaaggat cattaacctc actagtgttt tgagtctcca ggaagaaatt    1560
aatgagcagg gacatgaggt tctccgggag atgttgcata accactcctt cgtgggctgt    1620
gtgaatcctc agtgggcctt ggcacagcat caaaccaagt tataccttct caacaccacc    1680
aagcttagtg aagaactgtt ctaccagata ctcatttatg attttgccaa ttttggtgtt    1740
ctcaggttat cggagccagc accgctcttt gaccttgcca tgcttgcctt agatagtcca    1800
gagagtggct ggacagagga agatggtccc aaagaaggac ttgctgaata cattgttgag    1860
tttctgaaga agaaggctga gatgcttgca gactatttct ctttggaaat tgatgaggaa    1920
gggaacctga ttggattacc ccttctgatt gacaactatg tgcccccttt ggagggactg    1980
cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca aagtgtgata tacaaagtgt accaacataa gtgttggtag    2400
cacttaagac ttatacttgc cttctgatag tattccttta tacacagtgg attgattata    2460
aataaataga tgtgtcttaa cata                                           2484 hPMS2-134 protein (SEQ ID NO: 21)
MKQLPAATVR LLSSSQIITS VVSVVKELIE NSLDAGATSV DVKLENYGFD KIEVRDNGEG     60

IKAVDAPVMA MKYYTSKINS HEDLENLTTY GFRGEALGSI CCIAEVLITT RTAADNFSTQ    120

YVLDGSGHIL SQK                                                       133 hPMS2-134 cDNA (SEQ ID NO: 11)
cgaggcggat cgggtgttgc atccatggag cgagctgaga gctcgagtac agaacctgct     60
aaggccatca aacctattga tcggaagtca gtccatcaga tttgctctgg caggtggta    120 ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt     300 caagagtttg ccgacctaac tcaggttgaa actttggct ttcgggggga agctctgagc    360
tcactttgtg cactgagcga tgtcaccatt tctacctgcc acgcatcggc gaaggttgga    420 acttga                                                               426 hMSH6 (human cDNA) ACCESSION U28946 (SEQ ID NO: 22)
MSRQSTLYSFFPKSPALSDANKASARASREGGRAAAAPGASPSP

GGDAAWSEAGPGPRPLARSASPPKAKNLNGGLRRSVAPAAPTSCDFSPGDLVWAKMEG

YPWWPCLVYNHPFDGTFIREKGKSVRVHVQFFDDSPTRGWVSKRLLKPYTGSKSKEAQ

KGGHFYSAKPEILRAMQRADEALNKDKIKRLELAVCDEPSEPEEEEEMEVGTTYVTDK

SEEDNEIESEEEVQPKTQGSRRSSRQIKKRRVISDSESDIGGSDVEFKPDTKEEGSSD

EISSGVGDSESEGLNSPVKVARKRKRMVTGNGSLKRKSSRKETPSATKQATSISSETK

NTLRAFSAPQNSESQAHVSGGGDDSSRPTVWYHETLEWLKEEKRRDEHRRRPDHPDFD

ASTLYVPEDFLNSCTPGMRKWWQIKSQNFDLVICYKVGKEYELYHMDALIGVSELGLV

FMKGNWAHSGFPEIAFGRYSDSLVQKGYKVARVEQTETPEMMEARCRKMAHISKYDRV

VRREICRIITKGTQTYSVLEGDPSENYSKYLLSLKEKEEDSSGHTRAYGVCFVDTSLG

KFFIGQFSDDRHCSRFRTLVAHYPPVQVLFEKGNLSKETKTILKSSLSCSLQEGLIPG
```

-continued

SQFWDASKTLRTLLEEEYFREKLSDGIGVMLPQVLKGMTSESDSIGLTPGEKSELALS

ALGGCVFYLKKCLIDQELLSMANFEEYIPLDSDTVSTTRSGAIFTKAYQRMVLDAVTL

NNLEIFLNGTNGSTEGTLLERVDTCHTPFGKRLLKQWLCAPLCNHYAINDRLDAIEDL

MVVPDKISEVVELLKKLPDLERLLSKIHNVGSPLKSQNHPDSRAIMYEETTYSKKKII

DFLSALEGFKVMCKIIGIMEEVADGFKSKILKQVISLQTKNPEGRFPDLTVELNRWDT

AFDHEKARKTGLITPKAGFDSDYDQALADIRENEQSLLEYLEKQRNRIGCRTIVYWGI

GRNRYQLEIPENFTTRNLPEEYELKSTKKGCKRYWTKTIEKKLANLINAEERRDVSLK

DCMRRLFYNFDKNYKDWQSAVECIAVLDVLLCLANYSRGGDGPMCRPVILLPEDTPPF

LELKGSRHPCITKTFFGDDFIPNDILIGCEEEEQENGKAYCVLVTGPNMGGKSTLMRQ

AGLLAVMAQMGCYVPAEVCRLTPIDRVFTRLGASDRIMSGESTFFVELSETASILMHA

TAHSLVLVDELGRGTATFDGTAIANAVVKELAETIKCRTLFSTHYHSLVEDYSQNVAV

RLGHMACMVENECEDPSQETITFLYKFIKGACPKSYGFNAARLANLPEEVIQKGHRKA

REFEKMNQSLRLFREVCLASERSTVDAEAVHKLLTLIKEL"

hPMSR2 (human cDNA) ACCESSION U38964 (SEQ ID NO: 12)
```
   1 ggcgctccta cctgcaagtg gctagtgcca agtgctgggc cgccgctcct gccgtgcatg
  61 ttggggagcc agtacatgca ggtgggctcc acacggagag gggcgcagac ccggtgacag
 121 ggctttacct ggtacatcgc catggcgcaa ccaaagcaag agagggtggc cgcgtgccaga
 181 caccaacggt cggaaaccgc cagacaccaa cggtcggaaa ccgccaagac accaacgctc
 241 ggaaaccgcc agacaccaac gctcggaaac cgccagacac caaggctcgg aatccacgcc
 301 aggccacgac ggagggcgac tacctccctt ctgaccctgc tgctggcgtt cggaaaaaac
 361 gcagtccggt gtgctctgat tggtccaggc tctttgacgt cacggactcg acctttgaca
 421 gagccactag gcgaaaagga gacgggaa gtattttttc cgccccgccc ggaaagggtg
 481 gagcacaacg tcgaaagcag ccgttgggag cccaggagcc ggggcgcctg tgggagccgt
 541 ggagggaact ttcccagtcc ccgaggcgga tccggtgttg catccttgga gcgagctgag
 601 aactcgagta cagaacctgc taaggccatc aaacctattg atcggaagtc agtccatcag
 661 atttgctctg ggccggtggt accgagtcta aggccgaatg cggtgaagga gttagtagaa
 721 aacagtctgg atgctggtgc cactaatgtt gatctaaagc ttaaggacta tggagtggat
 781 ctcattgaag tttcaggcaa tggatgtggg gtagaagaag aaaacttcga aggctttact
 841 ctgaaacatc acacatgtaa gattcaagag tttgccgacc taactcaggt ggaaactttt
 901 ggctttcggg gggaagctct gagctcactt tgtgcactga gtgatgtcac catttctacc
 961 tgccgtgtat cagcgaaggt tgggactcga ctggtgtttg atcactatgg gaaaatcatc
1021 cagaaaaccc cctaccccg ccccagaggg atgacagtca gcgtgaagca gttatttct
1081 acgctacctg tgcaccataa agaatttcaa aggaatatta agaagaaacg tgcctgcttc
1141 cccttcgcct tctgccgtga ttgtcagttt cctgaggcct ccccagccat gcttcctgta
1201 cagcctgtag aactgactcc tagaagtacc ccaccccacc cctgctcctt ggaggacaac
1261 gtgatcactg tattcagctc tgtcaagaat ggtccaggtt cttctagatg atctgcacaa
1321 atggttcctc tcctccttcc tgatgtctgc cattagcatt ggaataaagt tcctgctgaa
1381 aatccaaaaa aaaaaaaaaa aaaaaaaa
``` hPMSR2 (human protein) ACCESSION U38964 (SEQ ID NO: 23)
MAQPKQERVARARHQRSETARHQRSETAKTPTLGNRQTPTLGNR

QTPRLGIHARPRRRATTSLLTLLLAFGKNAVRCALIGPGSLTSRTRPLTEPLGEKERR

EVFFPPRPERVEHNVESSRWEPRRRGACGSRGGNFPSPRGGSGVASLERAENSSTEPA

KAIKPIDRKSVHQICSGPVVPSLRPNAVKELVENSLDAGATNVDLKLKDYGVDLIEVS

GNGCGVEEENFEGFTLKHHTCKIQEFADLTQVETFGFRGEALSSLCALSDVTISTCRV

SAKVGTRLVFDHYGKIIQKTPYPRPRGMTVSVKQLFSTLPVHHKEFQRNIKKKRACFP

FAFCRDCQFPEASPAMLPVQPVELTPRSTPPHPCSLEDNVITVFSSVKNGPGSSR

HPMSR3 (human cDNA) ACCESSION U38979 (SEQ ID NO: 13)

```
   1 ttttttagaaa ctgatgttta ttttccatca accatttttc catgctgctt aagagaatat
  61 gcaagaacag cttaagacca gtcagtggtt gctcctaccc attcagtggc ctgagcagtg
 121 gggagctgca gaccagtctt ccgtggcagg ctgagcgctc cagtcttcag tagggaattg
 181 ctgaataggc acagagggca cctgtacacc ttcagaccag tctgcaacct caggctgagt
 241 agcagtgaac tcaggagcgg gagcagtcca ttcaccctga aattcctcct tggtcactgc
 301 cttctcagca gcagcctgct cttcttttc aatctcttca ggatctctgt agaagtacag
 361 atcaggcatg acctcccatg ggtgttcacg ggaaatggtg ccacgcatgc gcagaacttc
 421 ccgagccagc atccaccaca ttaaacccac tgagtgagct cccttgttgt tgcatgggat
 481 ggcaatgtcc acatagcgca gaggagaatc tgtgttacac agcgcaatgg taggtaggtt
 541 aacataagat gcctccgtga gaggcgaagg ggcggcggga cccgggcctg gcccgtatgt
 601 gtccttggcg gcctagacta ggccgtcgct gtatggtgag ccccagggag gcggatctgg
 661 gcccccagaa ggacacccgc ctggatttgc cccgtagccc ggcccgggcc cctcgggagc
 721 agaacagcct tggtgaggtg gacaggaggg gacctcgcga gcagacgcgc gcgccagcga
 781 cagcagcccc gccccggcct ctcgggagcc gggggggcaga ggctgcggag ccccaggagg
 841 gtctatcagc cacagtctct gcatgtttcc aagagcaaca ggaaatgaac acattgcagg
 901 ggccagtgtc attcaaagat gtggctgtgg atttcaccca ggaggagtgg cggcaactgg
 961 accctgatga agagatagca tacggggatg tgatgttgga aactacagc catctagttt
1021 ctgtggggta tgattatcac caagccaaac atcatcatgg agtggaggtg aaggaagtgg
1081 agcagggaga ggagccgtgg ataatggaag gtgaatttcc atgtcaacat agtccagaac
1141 ctgctaaggc catcaaacct attgatcgga agtcagtcca tcagatttgc tctgggccag
1201 tggtactgag tctaagcact gcagtgaagg agttagtaga aacagtctg gatgctggtg
1261 ccactaatat tgatctaaag cttaaggact atggagtgga tctcattgaa gtttcagaca
1321 atggatgtgg ggtagaagaa gaaaactttg aaggcttaat ctctttcagc tctgaaacat
1381 cacacatgta agattcaaga gtttgccgac ctaactgaag ttgaaacttt cggttttcag
1441 ggggaagctc tgagctcact gtgtgcactg agcgatgtca ccatttctac ctgccacgcg
1501 ttggtgaagg ttgggactcg actggtgttt gatcacgatg ggaaaatcat ccaggaaacc
1561 ccctacccc accccagagg gaccacagtc agcgtgaagc agttattttc tacgctacct
1621 gtgcgccata aggaatttca aaggaatatt aagaagacgt gcctgcttcc ccttcgcctt
1681 ctgccgtgat tgtcagtttc ctgaggcctc cccagccatg cttcctgtac agcctgcaga
1741 actgtgagtc aattaaacct ctttcttca taaattaaaa aaaaa
``` hPMSR3 (human protein) ACCESSION U38979 (SEQ ID NO: 24)
MCPWRPRLGRRCMVSPREADLGPQKDTRLDLPRSPARAPREQNS

LGEVDRRGPREQTRAPATAAPPRPLGSRGAEAAEPQEGLSATVSACFQEQQEMNTLQG

PVSFKDVAVDFTQEEWRQLDPDEKIAYGDVMLENYSHLVSVGYDYHQAKHHHGVEVKE

VEQGEEPWIMEGEFPCQHSPEPAKAIKPIDRKSVHQICSGPVVLSLSTAVKELVENSL

-continued

DAGATNIDLKLKDYGVDLIEVSDNGCGVEEENFEGLISFSSETSHM"

hPMSL9 (human cDNA) ACCESSION NM_005395 (SEQ ID NO: 14)
```
  1  atgtgtcctt ggcggcctag actaggccgt cgctgtatgg tgagccccag ggaggcggat
 61  ctgggccccc agaaggacac ccgcctggat ttgccccgta gccggcccg ggcccctcgg
121  gagcagaaca gccttggtga ggtggacagg aggggacctc gcgagcagac gcgcgcgcca
181  gcgacagcag ccccgccccg gcctctcggg agccgggggg cagaggctgc ggagccccag
241  gagggtctat cagccacagt ctctgcatgt tccaagagc aacaggaaat gaacacattg
301  cagggggccag tgtcattcaa agatgtggct gtggatttca cccaggagga gtggcggcaa
361  ctggaccctg atgagaagat agcatacggg gatgtgatgt tggagaacta cagccatcta
421  gtttctgtgg ggtatgatta tcaccaagcc aaacatcatc atggagtgga ggtgaaggaa
481  gtggagcagg gagaggagcc gtggataatg gaaggtgaat tccatgtca acatagtcca
541  gaacctgcta aggccatcaa acctattgat cggaagtcag tccatcagat ttgctctggg
601  ccagtggtac tgagtctaag cactgcagtg aaggagttag tagaaaacag tctggatgct
661  ggtgccacta atattgatct aaagcttaag gactatgag tggatctcat tgaagtttca
721  gacaatggat gtggggtaga agaagaaaac tttgaaggct taatctcttt cagctctgaa
781  acatcacaca tgtaa
``` hPMSL9 (human protein) ACCESSION NM_005395 (SEQ ID NO: 25)
MCPWRPRLGRRCMVSPREADLGPQKDTRLDLPRSPARAPREQNS

LGEVDRRGPREQTPAPATAAPPRPLGSRGAEAAEPQEGLSATVSACFQEQQEMNTLQG

PVSFKDVAVDFTQEEWRQLDPDEKIAYGDVMLENYSHLVSVGYDYHQAKHHHGVEVKE

VEQGEEPWIMEGEFPCQHSPEPAKAIKPIDRKSVHQICSGPVVLSLSTAVKELVENSL

DAGATNIDLKLKDYGVDLIEVSDNGCGVEEENFEGLISFSSETSHM"

---

We claim:

1. A method for generating a population of mismatch repair-proficient yeast with new output traits, comprising the steps of:
   growing a yeast cell comprising a gene of interest and a polynucleotide encoding a PMS2, wherein said PMS2 comprises an ATPase domain and has the ability to inhibit mismatch repair, to create a population of mutated, hypermutable yeast cells;
   selecting yeast cells having a mutation in the gene of interest; and
   restoring normal mismatch repair activity to the selected yeast cells.

2. The method of claim 1 wherein the yeast cell is exposed to a mutagen to increase the rate of mutation prior to the step of cultivating.

3. The method of claim 1 wherein the step of restoring normal mismatch repair activity comprises removing an inducer which regulates transcription of the polynucleotide encoding said PMS2 from the yeast cells.

4. The method of claim 1 wherein the step of restoring normal mismatch repair activity comprises excising the polynucleotide encoding said PMS2 by homologous recombination.

5. The method of claim 1 wherein the step of restoring normal mismatch repair activity involves inactivating the polynucleotide encoding said PMS2.

6. The method of claim 1 wherein the step of restoring normal mismatch repair activity comprises applying selection conditions to the yeast cells under which cells which have lost the polynucleotide encoding said PMS2 can grow but cells which harbor the dominant negative allele cannot grow.

7. The method of claim 1 wherein the step of restoring normal mismatch repair activity is performed subsequent to the step of cultivating under trait selection conditions.

8. The method of claim 2 wherein the step of restoring normal mismatch repair activity is performed subsequent to the step of exposing to a mutagen and subsequent to the step of cultivating under trait selection conditions.

9. The method of claim 2 wherein mutagen is ionizing radiation.

10. The method of claim 2 wherein the mutagen is ultraviolet irradiation.

11. The method of claim 1 wherein said PMS2 is PMS2-134, PMS2, PMSR2, or PMSR3.

12. A method for generating a genetically altered clonal yeast cell population comprising:
   introducing a polynucleotide encoding a PMS2, wherein said PMS2 comprises an ATPase domain and has the ability to inhibit mismatch repair, said polynucleotide operably linked to a promoter, in a population of yeast cells in culture, thereby inhibiting mismatch repair in said cells,
   separating said population into individual members of the population,
   identifying members of the population comprising a mutation in a gene of interest,
   restoring mismatch repair activity to said members of the population comprising a mutation in the gene of interest, and
   expanding said members comprising a mutation in the gene of interest,
   thereby generating a genetically altered clonal yeast cell population.

13. The method of claim 12 wherein the yeast cell is exposed to a mutagen to increase the rate of mutation prior to the step of cultivating.

14. The method of claim 12 wherein the step of restoring normal mismatch repair activity comprises removing an inducer which regulates transcription of the polynucleotide encoding said PMS2 from the yeast cells.

15. The method of claim 12 wherein the step of restoring normal mismatch repair activity comprises excising the polynucleotide encoding said PMS2 by homologous recombination.

16. The method of claim 12 wherein the step of restoring normal mismatch repair activity involves inactivating the polynucleotide encoding said PMS2.

17. The method of claim 12 wherein the step of restoring normal mismatch repair activity comprises applying selection conditions to the yeast cells under which cells which have lost the polynucleotide encoding said PMS2 can grow but cells which harbor the dominant negative allele cannot grow.

18. The method of claim 12 wherein the step of restoring normal mismatch repair activity is performed subsequent to the step of cultivating under trait selection conditions.

19. The method of claim 13 wherein the step of restoring normal mismatch repair activity is performed subsequent to the step of exposing to a mutagen and subsequent to the step of cultivating under trait selection conditions.

20. The method of claim 13 wherein mutagen is ionizing radiation.

21. The method of claim 13 wherein the mutagen is ultraviolet (UV) irradiation.

22. The method of claim 12 wherein said PMS2 is PMS2-134, PMS2, PMSR2, or PMSR3.

* * * * *

SEQUENCE LISTING

```
<160> NUMBER OF SEQ ID NOS: 25

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
acgcatatgg agcgagctga gagctcgagt                                     30

<210> SEQ ID NO 2
<211> LENGTH: 75
<212> TYPE: DNA
<213> ORGANISM: Artificial Sequence
<220> FEATURE:
<223> OTHER INFORMATION: PCR primer

<400> SEQUENCE: 2
gaattcttat cacgtagaat cgagaccgag gagagggtta gggataggct taccagttcc    60
aaccttcgcc gatgc                                                     75

<210> SEQ ID NO 3
<211> LENGTH: 27
```

```
<212> TYPE: DNA
<213> ORGANISM: Artificial Sequence
<220> FEATURE:
<223> OTHER INFORMATION: PCR primer

<400> SEQUENCE: 3
acgcatatgt gtccttggcg gcctaga                                          27

<210> SEQ ID NO 4
<211> LENGTH: 75
<212> TYPE: DNA
<213> ORGANISM: Artificial Sequence
<220> FEATURE:
<223> OTHER INFORMATION: PCR primer

<400> SEQUENCE: 4
gaattcttat tacgtagaat cgagaccgag gagagggtta gggataggct tacccatgtg      60
tgatgtttca gagct                                                      75

<210> SEQ ID NO 5
<211> LENGTH: 3218
<212> TYPE: DNA
<213> ORGANISM: Saccharomyces cerevisiae

<400> SEQUENCE: 5
aaataggaat gtgataccttc tattgcatg caaagatagt gtaggaggcg ctgctattgc      60
caaagacttt tgagaccgct tgctgtttca ttatagttga ggagttctcg aagacgagaa     120
attagcagtt ttcggtgttt agtaatcgcg ctagcatgct aggacaattt aactgcaaaa     180
ttttgatacg atagtgatag taaatggaag gtaaaaataa catagaccta tcaataagca     240
atgtctctca gaataaaagc acttgatgca tcagtggtta acaaaattgc tgcaggtgag     300
atcataatat cccccgtaaa tgctctcaaa gaaatgatgg agaattccat cgatgcgaat     360
gctacaatga ttgatattct agtcaaggaa ggaggaatta aggtacttca ataacagat      420 aacggatctg gaattaataa agcagacctg ccaatcttat gtgagcgatt cacgacgtcc     480
aaattacaaa aattcgaaga tttgagtcag attcaaacgt atggattccg aggagaagct     540
ttagccagta tctcacatgt ggcaagagtc acagtaacga caaaagttaa agaagacaga     600
tgtgcatgga gagtttcata tgcagaaggt aagatgttgg aaagccccaa acctgttgct     660
ggaaaagacg gtaccacgat cctagttgaa gaccttttt tcaatattcc ttctagatta     720
agggccttga ggtcccataa tgatgaatac tctaaaatat tagatgttgt cgggcgatac     780
gccattcatt ccaaggacat tggcttttct tgtaaaaagt tcggagactc taattattct     840
ttatcagtta aaccttcata tacagtccag gataggatta ggactgtgtt caataaatct     900
gtggcttcga atttaattac ttttcatatc agcaaagtag aagatttaaa cctggaaagc     960
gttgatggaa aggtgtgtaa tttgaatttc atatccaaaa agtccatttc attaattttt    1020
ttcattaata atagactagt gacatgtgat cttctaagaa gagctttgaa cagcgtttac    1080
tccaattatc tgccaaaggg cttcagacct tttatttatt tgggaattgt tatagatccg    1140
gcggctgttg atgttaacgt tcacccgaca aagagagagg ttcgtttcct gagccaagat    1200
gagatcatag agaaaatcgc caatcaattg cacgccgaat tatctgccat tgatacttca    1260
cgtactttca aggcttcttc aatttcaaca acaagccag agtcattgat accatttaat    1320
gacaccatag aaagtgatag gaataggaag agtctccgac aagcccaagt ggtagagaat    1380
tcatatacga cagccaatag tcaactaagg aaagcgaaaa gacaagagaa taaactagtc    1440
```

-continued

```
agaatagatg cttcacaagc taaaattacg tcatttttat cctcaagtca acagttcaac    1500
tttgaaggat cgtctacaaa gcgacaactg agtgaaccca aggtaacaaa tgtaagccac    1560
tcccaagagg cagaaaagct gacactaaat gaaagcgaac aaccgcgtga tgccaataca    1620
atcaatgata atgacttgaa ggatcaacct aagaagaaac aaaagttggg ggattataaa    1680
gttccaagca ttgccgatga cgaaaagaat gcactcccga tttcaaaaga cgggtatatt    1740
agagtaccta aggagcgagt taatgttaat cttacgagta tcaagaaatt gcgtgaaaaa    1800
gtagatgatt cgatacatcg agaactaaca gacattttg caaatttgaa ttacgttggg     1860
gttgtagatg aggaaagaag attagccgct attcagcatg acttaaagct ttttttaata    1920
gattacggat ctgtgtgcta tgagctattc tatcagattg gtttgacaga cttcgcaaac    1980
tttggtaaga taaacctaca gagtacaaat gtgtcagatg atatagtttt gtataatctc    2040
ctatcagaat ttgacgagtt aaatgacgat gcttccaaag aaaaaataat tagtaaaata    2100
tgggacatga gcagtatgct aaatgagtac tattccatag aattggtgaa tgatggtcta    2160
gataatgact taaagtctgt gaagctaaaa tctctaccac tacttttaaa aggctacatt    2220
ccatctctgg tcaagttacc attttttata tatcgcctgg gtaaagaagt tgattgggag    2280
gatgaacaag agtgtctaga tggtatttta agagagattg cattactcta tatacctgat    2340
atggttccga aagtcgatac actcgatgca tcgttgtcag aagacgaaaa agcccagttt    2400
ataaatagaa aggaacacat atcctcatta ctagaacacg ttctcttccc ttgtatcaaa    2460
cgaaggttcc tggcccctag acacattctc aaggatgtcg tggaaatagc caaccttcca    2520
gatctataca agtttttga gaggtgttaa ctttaaaacg ttttggctgt aataccaaag     2580
tttttgttta tttcctgagt gtgattgtgt ttcatttgaa agtgtatgcc cttccttta    2640 acgattcatc cgcgagattt caaggatat gaaatatggt tgcagttagg aaagtatgtc     2700
agaaatgtat attcggattg aaactcttct aatagttctg aagtcacttg gttccgtatt    2760
gttttcgtcc tcttcctcaa gcaacgattc ttgtctaagc ttattcaacg gtaccaaaga    2820
cccgagtcct tttatgagag aaaacatttc atcattttc aactcaatta tcttaatatc     2880
attttgtagt attttgaaaa caggatggta aaacgaatca cctgaatcta gaagctgtac    2940
cttgtcccat aaaagtttta atttactgag cctttcggtc aagtaaacta gtttatctag    3000
ttttgaaccg aatattgtgg gcagatttgc agtaagttca gttagatcta ctaaaagttg    3060
tttgacagca gccgattcca caaaaatttg gtaaaaggag atgaaagaga cctcgcgcgt    3120
aatggtttgc atcaccatcg gatgtctgtt gaaaaactca cttttttgcat ggaagttatt    3180 aacaataaga ctaatgatta ccttagaata atgtataa                            3218
```

<210> SEQ ID NO 6
<211> LENGTH: 3056
<212> TYPE: DNA
<213> ORGANISM: Mus musculus

<400> SEQUENCE: 6

```
gaattccggt gaaggtcctg aagaatttcc agattcctga gtatcattgg aggagacaga     60
taacctgtcg tcaggtaacg atggtgtata tgcaacagaa atgggtgttc ctggagacgc    120
gtcttttccc gagagcggca ccgcaactct cccgcggtga ctgtgactgg aggagtcctg    180
catccatgga gcaaaccgaa ggcgtgagta cagaatgtgc taaggccatc aagcctattg    240
atgggaagtc agtccatcaa atttgttctg ggcaggtgat actcagttta agcaccgctg    300
tgaaggagtt gatagaaaat agtgtagatg ctggtgctac tactattgat ctaaggctta    360
```

-continued

```
aagactatgg ggtggacctc attgaagttt cagacaatgg atgtggggta gaagaagaaa      420
actttgaagg tctagctctg aaacatcaca catctaagat tcaagagttt gccgacctca      480
cgcaggttga aactttcggc tttcgggggg aagctctgag ctctctgtgt gcactaagtg      540
atgtcactat atctacctgc cacgggtctg caagcgttgg gactcgactg gtgtttgacc      600
ataatgggaa aatcacccag aaaactccct accccgacc taaaggaacc acagtcagtg       660
tgcagcactt attttataca ctacccgtgc gttacaaaga gtttcagagg aacattaaaa     720
aggagtattc caaaatggtg caggtcttac aggcgtactg tatcatctca gcaggcgtcc     780
gtgtaagctg cactaatcag ctcggacagg ggaagcggca cgctgtggtg tgcacaagcg    840
gcacgtctgg catgaaggaa aatatcgggt ctgtgtttgg ccagaagcag ttgcaaagcc     900
tcattccttt tgttcagctg cccctagtg acgctgtgtg tgaagagtac ggcctgagca      960
cttcaggacg ccacaaaacc ttttctacgt ttcgggcttc atttcacagt gcacgcacgg    1020
cgccgggagg agtgcaacag acaggcagtt tttcttcatc aatcagaggc cctgtgaccc   1080
agcaaaggtc tctaagcttg tcaatgaggt tttatcacat gtataaccgg catcagtacc    1140
catttgtcgt ccttaacgtt tccgttgact cagaatgtgt ggatattaat gtaactccag   1200
ataaaaggca aattctacta caagaagaga agctattgct ggccgtttta aagacctcct   1260
tgataggaat gtttgacagt gatgcaaaca agcttaatgt caaccagcag ccactgctag   1320
atgttgaagg taacttagta aagctgcata ctgcagaact agaaaagcct gtgccaggaa   1380
agcaagataa ctctccttca ctgaagagca cagcagacga gaaaagggta gcatccatct   1440
ccaggctgag agaggccttt tctcttcatc ctactaaaga gatcaagtct aggggtccag   1500
agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaaagactca gggctcagca   1680
gcacctcagc tggctctgag gaagagttca gcaccccaga agtggccagt agctttagca   1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt caccccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt tacagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga aagaggacct cttcctggtg gaccagcatg   2280
ctgcggatga aagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatggctttg actttgtcat tgatgaggat gctccagtca   2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacgcgc    2640 tcaatgcgag cgagatgaag aagctcatca cccacatggg tgagatggac cacccctgga   2700
```

| | |
|---|---|
| actgccccca cggcaggcca accatgaggc acgttgccaa tctggatgtc atctctcaga | 2760 |
| actgacacac cccttgtagc atagagttta ttacagattg ttcggtttgc aaagagaagg | 2820 |
| ttttaagtaa tctgattatc gttgtacaaa aattagcatg ctgctttaat gtactggatc | 2880 |
| catttaaaag cagtgttaag gcaggcatga tggagtgttc ctctagctca gctacttggg | 2940 |
| tgatccggtg ggagctcatg tgagcccagg actttgagac cactccgagc cacattcatg | 3000 |
| agactcaatt caaggacaaa aaaaaaaaga tattttgaa gccttttaaa aaaaaa | 3056 |

<210> SEQ ID NO 7
<211> LENGTH: 2771
<212> TYPE: DNA
<213> ORGANISM: Homo sapiens

<400> SEQUENCE: 7

| | |
|---|---|
| cgaggcggat cgggtgttgc atccatggag cgagctgaga gctcgagtac agaacctgct | 60 |
| aaggccatca aacctattga tcggaagtca gtccatcaga tttgctctgg gcaggtggta | 120 |
| ctgagtctaa gcactgcggt aaaggagtta gtagaaaaca gtctggatgc tggtgccact | 180 |
| aatattgatc taaagcttaa ggactatgga gtggatctta ttgaagtttc agacaatgga | 240 |
| tgtggggtag aagaagaaaa cttcgaaggc ttaactctga acatcacac atctaagatt | 300 |
| caagagtttg ccgacctaac tcaggttgaa acttttggct tcgggggga agctctgagc | 360 |
| tcactttgtg cactgagcga tgtcaccatt tctacctgcc acgcatcggc gaaggttgga | 420 |
| actcgactga tgtttgatca caatgggaaa attatccaga aaaccccta ccccgcccc | 480 |
| agagggacca cagtcagcgt gcagcagtta ttttccacac tacctgtgcg ccataaggaa | 540 |
| tttcaaagga atattaagaa ggagtatgcc aaaatggtcc aggtcttaca tgcatactgt | 600 |
| atcatttcag caggcatccg tgtaagttgc accaatcagc ttggacaagg aaaacgacag | 660 |
| cctgtggtat gcacaggtgg aagccccagc ataaaggaaa atatcggctc tgtgtttggg | 720 |
| cagaagcagt tgcaaagcct cattcctttt gttcagctgc ccctagtga ctccgtgtgt | 780 |
| gaagagtacg gtttgagctg ttcggatgct ctgcataatc tttttacat ctcaggtttc | 840 |
| atttcacaat gcacgcatgg agttggaagg agttcaacag acagacagtt tttctttatc | 900 |
| aaccggcggc cttgtgaccc agcaaaggtc tgcagactcg tgaatgaggt ctaccacatg | 960 |
| tataatcgac accagtatcc atttgttgtt cttaacattt ctgttgattc agaatgcgtt | 1020 |
| gatatcaatg ttactccaga taaaaggcaa attttgctac aagaggaaaa gcttttgttg | 1080 |
| gcagttttaa agacctcttt gataggaatg tttgatagtg atgtcaacaa gctaaatgtc | 1140 |
| agtcagcagc cactgctgga tgttgaaggt aacttaataa aaatgcatgc agcggatttg | 1200 |
| gaaaagccca tggtagaaaa gcaggatcaa tccccttcat taaggactgg agaagaaaaa | 1260 |
| aaagacgtgt ccatttccag actgcgagag ccttttctc ttcgtcacac aacagagaac | 1320 |
| aagcctcaca gcccaaagac tccagaacca agaaggagcc ctctaggaca gaaaggggt | 1380 |
| atgctgtctt ctagcacttc aggtgccatc tctgacaaag gcgtcctgag acctcagaaa | 1440 |
| gaggcagtga gttccagtca cggacccagt gaccctacgg acagagcgga ggtggagaag | 1500 |
| gactcggggc acggcagcac ttccgtggat tctgaggggt tcagcatccc agacacgggc | 1560 |
| agtcactgca gcagcgagta tgcggccagc tccccagggg acaggggctc gcaggaacat | 1620 |
| gtggactctc aggagaaagc gcctgaaact gacgactctt tttcagatgt ggactgccat | 1680 |
| tcaaaccagg aagataccgg atgtaaattt cgagttttgc ctcagccaac taatctcgca | 1740 |
| accccaaaca caaagcgttt taaaaaagaa gaattctttt ccagttctga catttgtcaa | 1800 |

```
aagttagtaa atactcagga catgtcagcc tctcaggttg atgtagctgt gaaaattaat    1860
aagaaagttg tgcccctgga cttttctatg agttctttag ctaaacgaat aaagcagtta    1920
catcatgaag cacagcaaag tgaaggggaa cagaattaca ggaagtttag ggcaaagatt    1980
tgtcctggag aaaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgattc cttgccaact     2340 agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520 cacatgggg agatggacca cccctggaac tgtccccatg gaaggccaac catgagacac      2580
atcgccaacc tgggtgtcat ttctcagaac tgaccgtagt cactgtatgg aataattggt    2640
tttatcgcag atttttatgt tttgaaagac agagtcttca ctaaccttt ttgttttaaa     2700 atgaaacctg ctacttaaaa aaaatacaca tcacacccat ttaaaagtga tcttgagaac    2760
cttttcaaac c                                                         2771

<210> SEQ ID NO 8
<211> LENGTH: 3063
<212> TYPE: DNA
<213> ORGANISM: Homo sapiens

<400> SEQUENCE: 8
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctccttcaa      120 gttctcagat catcacttcg gtggtcagtg ttgtaaaaga gcttattgaa aactccttgg     180
atgctggtgc cacaagcgta gatgttaaac tggagaacta tggatttgat aaaattgagg    240
tgcgagataa cggggagggt atcaaggctg ttgatgcacc tgtaatggca atgaagtact    300
acacctcaaa aataaatagt catgaagatc ttgaaaattt gacaacttac ggttttcgtg    360
gagaagcctt ggggtcaatt tgttgtatag ctgaggtttt aattacaaca gaacggctg     420 ctgataattt tagcacccag tatgttttag atggcagtgg ccacatactt tctcagaaac    480
cttcacatct tggtcaaggt acaactgtaa ctgctttaag attatttaag aatctacctg    540
taagaaagca gttttactca actgcaaaaa aatgtaaaga tgaaataaaa aagatccaag    600
atctcctcat gagctttggt atccttaaac ctgacttaag gattgtcttt gtacataaca    660
aggcagttat ttggcagaaa agcagagtat cagatcacaa gatggctctc atgtcagttc    720
tggggactgc tgttatgaac aatatggaat cctttcagta ccactctgaa gaatctcaga    780
tttatctcag tggatttctt ccaaagtgtg atgcagacca ctctttcact agtctttcaa    840
caccagaaag aagtttcatc ttcataaaca gtcgaccagt acatcaaaaa gatatcttaa    900
agttaatccg acatcattac aatctgaaat gcctaaagga atctactcgt tgtatcctg    960 ttttctttct gaaatcgat gttcctacag ctgatgttga tgtaaattta acaccagata    1020
aaagccaagt attattacaa aataaggaat ctgttttaat tgctcttgaa aatctgatga    1080
```

```
cgacttgtta tggaccatta cctagtacaa attcttatga aaataataaa acagatgttt      1140
ccgcagctga catcgttctt agtaaaacag cagaaacaga tgtgcttttt aataaagtgg      1200
aatcatctgg aaagaattat tcaaatgttg atacttcagt cattccattc caaaatgata      1260
tgcataatga tgaatctgga aaaaacactg atgattgttt aaatcaccag ataagtattg      1320
gtgactttgg ttatggtcat tgtagtagtg aaatttctaa cattgataaa aacactaaga      1380
atgcatttca ggacatttca atgagtaatg tatcatggga gaactctcag acggaatata      1440
gtaaaacttg ttttataagt tccgttaagc acacccagtc agaaaatggc aataaagacc      1500
atatagatga gagtggggaa aatgaggaag aagcaggtct tgaaaactct tcggaaattt      1560
ctgcagatga gtggagcagg ggaaatatac ttaaaaattc agtgggagag aatattgaac      1620
ctgtgaaaat tttagtgcct gaaaaaagtt taccatgtaa agtaagtaat aataattatc      1680
caatccctga acaaatgaat cttaatgaag attcatgtaa caaaaaatca aatgtaatag      1740
ataataaatc tggaaaagtt acagcttatg atttacttag caatcgagta atcaagaaac      1800
ccatgtcagc aagtgctctt tttgttcaag atcatcgtcc tcagtttctc atagaaaatc      1860
ctaagactag tttagaggat gcaacactac aaattgaaga actgtggaag acattgagtg      1920
aagaggaaaa actgaaatat gaagagaagg ctactaaaga cttggaacga tacaatagtc      1980
aaatgaagag agccattgaa caggagtcac aaatgtcact aaaagatggc agaaaaaaga      2040 taaacccac cagcgcatgg aatttggccc agaagcacaa gttaaaaacc tcattatcta      2100
atcaaccaaa acttgatgaa ctccttcagt cccaaattga aaaagaagg agtcaaaata      2160 ttaaaatggt acagatcccc ttttctatga aaaacttaaa aataaatttt aagaaacaaa      2220
acaaagttga cttagaagag aaggatgaac cttgcttgat ccacaatctc aggtttcctg      2280
atgcatggct aatgacatcc aaaacagagg taatgttatt aaatccatat agagtagaag      2340
aagccctgct atttaaaaga cttcttgaga atcataaact tcctgcagag ccactggaaa      2400
agccaattat gttaacagag agtctttta atggatctca ttatttagac gttttatata      2460
aaatgacagc agatgaccaa agatacagtg gatcaactta cctgtctgat cctcgtctta      2520
cagcgaatgg tttcaagata aaattgatac caggagtttc aattactgaa aattacttgg      2580
aaatagaagg aatggctaat tgtctcccat tctatggagt agcagattta aaagaaattc      2640
ttaatgctat attaaacaga aatgcaaagg aagtttatga atgtagacct cgcaaagtga      2700
taagttattt agagggagaa gcagtgcgtc tatccagaca attacccatg tacttatcaa      2760
aagaggacat ccaagacatt atctacagaa tgaagcacca gttggaaat gaaattaaag      2820 agtgtgttca tggtcgccca ttttttcatc atttaaccta tcttccagaa actacatgat      2880
taaatatgtt taagaagatt agttaccatt gaaattggt ctgtcataaa acagcatgag      2940 tctggttta aattatcttt gtattatgtg tcacatggtt attttttaaa tgaggattca      3000
ctgacttgtt tttatattga aaaagttcc acgtattgta gaaaacgtaa ataaactaat      3060
aac                                                                   3063
```

<210> SEQ ID NO 9
<211> LENGTH: 3145
<212> TYPE: DNA
<213> ORGANISM: Homo sapiens

<400> SEQUENCE: 9

```
ggcgggaaac agcttagtgg gtgtggggtc gcgcattttc ttcaaccagg aggtgaggag        60
gtttcgacat ggcggtgcag ccgaaggaga cgctgcagtt ggagagcgcg gccgaggtcg       120
```

```
gcttcgtgcg cttctttcag ggcatgccgg agaagccgac caccacagtg cgccttttcg       180
accgggcga cttctatacg gcgcacggcg aggacgcgct gctggccgcc cgggaggtgt        240
tcaagaccca gggggtgatc aagtacatgg ggccggcagg agcaaagaat ctgcagagtg       300
ttgtgcttag taaatgaat tttgaatctt ttgtaaaaga tcttcttctg gttcgtcagt        360
atagagttga agtttataag aatagagctg gaaataaggc atccaaggag aatgattggt       420
atttggcata taaggcttct cctggcaatc tctctcagtt tgaagacatt ctctttggta       480
acaatgatat gtcagcttcc attggtgttg tgggtgttaa aatgtccgca gttgatggcc       540
agagacaggt tggagttggg tatgtggatt ccatacagag gaaactagga ctgtgtgaat       600
tccctgataa tgatcagttc tccaatcttg aggctctcct catccagatt ggaccaaagg       660
aatgtgtttt acccggagga gagactgctg agacatggg gaaactgaga cagataattc         720
aaagaggagg aattctgatc acagaaagaa aaaaagctga cttttccaca aaagacattt       780
atcaggacct caaccggttg ttgaaaggca aaagggaga gcagatgaat agtgctgtat          840
tgccagaaat ggagaatcag gttgcagttt catcactgtc tgcggtaatc aagttttag         900
aactcttatc agatgattcc aactttggac agtttgaact gactactttt gacttcagcc       960
agtatatgaa attggatatt gcagcagtca gagcccttaa ccttttttcag ggttctgttg      1020
aagataccac tggctctcag tctctggctg ccttgctgaa taagtgtaaa accccctcaag     1080
gacaaagact tgttaaccag tggattaagc agcctctcat ggataagaac agaatagagg       1140
agagattgaa tttagtggaa gcttttgtag aagatgcaga attgaggcag actttacaag       1200
aagatttact tcgtcgattc ccagatctta accgacttgc caagaagttt caaagacaag       1260
cagcaaactt acaagattgt taccgactct atcagggtat aaatcaacta cctaatgtta       1320
tacaggctct ggaaaaacat gaaggaaaac accagaaatt attgttggca gttttttgtga     1380
ctcctcttac tgatcttcgt tctgacttct ccaagtttca ggaaatgata gaaacaactt      1440
tagatatgga tcaggtggaa aaccatgaat tccttgtaaa accttcattt gatcctaatc      1500
tcagtgaatt aagagaaata atgaatgact tggaaaagaa gatgcagtca acattaataa      1560
gtgcagccag agatcttggc ttggaccctg gcaaacagat taaactggat tccagtgcac      1620
agtttggata ttactttcgt gtaacctgta aggaagaaaa agtccttcgt aacaataaaa      1680
actttagtac tgtagatatc cagaagaatg gtgttaaatt taccaacagc aaattgactt      1740
ctttaaatga agagtatacc aaaaataaaa cagaatatga agagcccag gatgccattg       1800
ttaaagaaat tgtcaatatt tcttcaggct atgtagaacc aatgcagaca ctcaatgatg       1860
tgttagctca gctagatgct gttgtcagct ttgctcacgt gtcaaatgga gcacctgttc      1920
catatgtacg accagccatt ttggagaaag gacaaggaag aattatatta aaagcatcca      1980
ggcatgcttg tgttgaagtt caagatgaaa ttgcatttat tcctaatgac gtatactttg      2040
aaaaagataa acagatgttc cacatcatta ctggccccaa tatgggaggt aaatcaacat      2100
atattcgaca aactggggtg atagtactca tggcccaaat tgggtgtttt tgtgccatgtg     2160
agtcagcaga agtgtccatt gtggactgca tcttagcccg agtaggggct ggtgacagtc      2220
aattgaaagg agtctccacg ttcatggctg aaatgttgga aactgcttct atcctcaggt      2280
ctgcaaccaa agattcatta ataatcatag atgaattggg aagaggaact tctacctacg      2340
atggatttgg gttagcatgg gctatatcag aatacattgc aacaaagatt ggtgctttt      2400
gcatgtttgc aacccatttt catgaactta ctgccttggc caatcagata ccaactgtta      2460
```

```
ataatctaca tgtcacagca ctcaccactg aagagacctt aactatgctt tatcaggtga    2520
agaaaggtgt ctgtgatcaa agttttggga ttcatgttgc agagcttgct aatttccta     2580 agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg ccctttactg    2760
aaatgtcaga agaaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc tttttccata gtgttaactg tcagtgccca tgggctatca acttaataag    3000
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                          3145

<210> SEQ ID NO 10
<211> LENGTH: 2484
<212> TYPE: DNA
<213> ORGANISM: Homo sapiens

<400> SEQUENCE: 10
cttggctctt ctggcgccaa aatgtcgttc gtggcagggg ttattcggcg gctggacgag      60
acagtggtga accgcatcgc ggcgggggaa gttatccagc ggccagctaa tgctatcaaa     120
gagatgattg agaactgttt agatgcaaaa tccacaagta ttcaagtgat tgttaaagag     180
ggaggcctga gttgattca gatccaagac aatggcaccg ggatcaggaa agaagatctg     240
gatattgtat gtgaaaggtt cactactagt aaactgcagt cctttgagga tttagccagt     300
atttctacct atggctttcg aggtgaggct ttggccagca taagccatgt ggctcatgtt     360
actattacaa cgaaaacagc tgatggaaag tgtgcataca gagcaagtta ctcagatgga     420
aaactgaaag cccctcctaa accatgtgct ggcaatcaag ggacccagat cacggtggag     480
gacctttttt acaacatagc cacgaggaga aaagctttaa aaaatccaag tgaagaatat     540
gggaaaattt tggaagttgt tggcaggtat tcagtacaca atgcaggcat tagtttctca     600
gttaaaaaac aaggagagac agtagctgat gttaggacac tacccaatgc ctcaaccgtg     660
gacaatattc gctccatctt tggaaatgct gttagtcgag aactgataga aattggatgt     720
gaggataaaa ccctagcctt caaaatgaat ggttacatat ccaatgcaaa ctactcagtg     780
aagaagtgca tcttcttact cttcatcaac catcgtctgg tagaatcaac ttccttgaga     840
aaagccatag aaacagtgta tgcagcctat ttgcccaaaa acacacaccc attcctgtac     900
ctcagtttag aaatcagtcc ccagaatgtg atgttaatg tgcaccccac aaagcatgaa     960
gttcacttcc tgcacgagga gagcatcctg gagcgggtgc agcagcacat cgagagcaag    1020
ctcctgggct ccaattcctc caggatgtac ttcacccaga ctttgctacc aggacttgct    1080
ggcccctctg gggagatggt taaatccaca acaagtctga cctcgtcttc tacttctgga    1140
agtagtgata aggtctatgc ccaccagatg gttcgtacag attcccggga acagaagctt    1200
gatgcatttc tgcagcctct gagcaaaccc ctgtccagtc agcccaggc cattgtcaca    1260 gaggataaga cagatatttc tagtggcagg gctaggcagc aagatgagga gatgcttgaa    1320
ctcccagccc ctgctgaagt ggctgccaaa aatcagagct ggagggga tacaacaaag    1380 gggacttcag aaatgtcaga gaagagagga cctacttcca gcaaccccag aaagagacat    1440
```

```
cgggaagatt ctgatgtgga atggtggaa gatgattccc gaaaggaaat gactgcagct    1500 tgtaccccc ggagaaggat cattaacctc actagtgttt tgagtctcca ggaagaaatt    1560
aatgagcagg gacatgaggt tctccgggag atgttgcata accactcctt cgtgggctgt    1620
gtgaatcctc agtgggcctt ggcacagcat caaaccaagt tataccttct caacaccacc    1680
aagcttagtg aagaactgtt ctaccagata ctcatttatg attttgccaa ttttggtgtt    1740
ctcaggttat cggagccagc accgctcttt gaccttgcca tgcttgcctt agatagtcca    1800
gagagtggct ggacagagga agatggtccc aaagaaggac ttgctgaata cattgttgag    1860
tttctgaaga agaaggctga gatgcttgca gactattct ctttggaaat tgatgaggaa    1920
gggaacctga ttggattacc ccttctgatt gacaactatg tgcccccttt ggagggactg    1980
cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caagtctttt    2280
gagaggtgtt aaatatggtt atttatgcac tgtgggatgt gttcttcttt ctctgtattc    2340
cgatacaaag tgttgtatca aagtgtgata tacaaagtgt accaacataa gtgttggtag    2400
cacttaagac ttatacttgc cttctgatag tattcctta tacacagtgg attgattata    2460
aataaataga tgtgtcttaa cata                                          2484

<210> SEQ ID NO 11
<211> LENGTH: 426
<212> TYPE: DNA
<213> ORGANISM: Homo sapiens

<400> SEQUENCE: 11
cgaggcggat cgggtgttgc atccatggag cgagctgaga gctcgagtac agaacctgct     60
aaggccatca aacctattga tcggaagtca gtccatcaga tttgctctgg gcaggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt    300 caagagtttg ccgacctaac tcaggttgaa acttttggct tcggggggga agctctgagc    360
tcactttgtg cactgagcga tgtcaccatt tctacctgcc acgcatcggc gaaggttgga    420
acttga                                                              426

<210> SEQ ID NO 12
<211> LENGTH: 1408
<212> TYPE: DNA
<213> ORGANISM: Homo sapiens

<400> SEQUENCE: 12
ggcgctccta cctgcaagtg ctagtgccaa gtgctgggc cgccgctcct gccgtgcatg     60
ttggggagcc agtacatgca ggtgggctcc acacggagag gggcgcagac ccggtgacag    120
ggctttacct ggtacatcgg catggcgcaa ccaaagcaag agagggtggc gcgtgccaga    180
caccaacggt cggaaaccgc cagacaccaa cggtcggaaa ccgccaagac accaacgctc    240
ggaaaccgcc agacaccaac gctcggaaac cgccagacac caaggctcgg aatccacgcc    300
```

```
aggccacgac ggagggcgac tacctcccct ctgaccctgc tgctggcgtt cggaaaaaac    360
gcagtccggt gtgctctgat tggtccaggc tctttgacgt cacggactcg acctttgaca    420
gagccactag gcgaaaagga gagacgggaa gtattttttc cgccccgccc ggaaagggtg    480
gagcacaacg tcgaaagcag ccgttgggag cccaggaggc ggggcgcctg tgggagccgt    540
ggagggaact ttcccagtcc ccgaggcgga tccggtgttg catccttgga gcagctgag    600 aactcgagta cagaacctgc taaggccatc aaacctattg atcggaagtc agtccatcag    660
atttgctctg gccggtggt accgagtcta aggccgaatg cggtgaagga gttagtagaa    720
aacagtctgg atgctggtgc cactaatgtt gatctaaagc ttaaggacta tggagtggat    780
ctcattgaag tttcaggcaa tggatgtggg gtagaagaag aaaacttcga aggctttact    840
ctgaaacatc acacatgtaa gattcaagag tttgccgacc taactcaggt ggaaactttt    900
ggctttcggg gggaagctct gagctcactt tgtgcactga gtgatgtcac catttctacc    960
tgccgtgtat cagcgaaggt tgggactcga ctggtgtttg atcactatgg gaaaatcatc    1020
cagaaaaccc cctacccccg ccccagaggg atgacagtca gcgtgaagca gttattttct    1080
acgctacctg tgcaccataa agaatttcaa aggaatatta agaagaaacg tgcctgcttc    1140
cccttcgcct tctgccgtga ttgtcagttt cctgaggcct ccccagccat gcttcctgta    1200
cagcctgtag aactgactcc tagaagtacc ccaccccacc cctgctcctt ggaggacaac    1260
gtgatcactg tattcagctc tgtcaagaat ggtccaggtt cttctagatg atctgcacaa    1320
atggttcctc cctccttcc tgatgtctgc cattagcatt ggaataaagt tcctgctgaa    1380
aatccaaaaa aaaaaaaaaa aaaaaaaa                                      1408
```

<210> SEQ ID NO 13
<211> LENGTH: 1785
<212> TYPE: DNA
<213> ORGANISM: Homo sapiens

<400> SEQUENCE: 13

```
tttttagaaa ctgatgttta ttttccatca accatttttc catgctgctt aagagaatat     60
gcaagaacag cttaagacca gtcagtggtt gctcctaccc attcagtggc ctgagcagtg    120
gggagctgca gaccagtctt ccgtggcagg ctgagcgctc cagtcttcag tagggaattg    180
ctgaataggc acagagggca cctgtacacc ttcagaccag tctgcaacct caggctgagt    240
agcagtgaac tcaggagcgg gagcagtcca ttcaccctga aattcctcct tggtcactgc    300
cttctcagca gcagcctgct cttcttttttc aatctcttca ggatctctgt agaagtacag    360
atcaggcatg acctcccatg ggtgttcacg ggaaatggtg ccacgcatgc gcagaacttc    420
ccgagccagc atccaccaca ttaaacccac tgagtgagct cccttgttgt tgcatgggat    480
ggcaatgtcc acatagcgca gaggagaatc tgtgttacac agcgcaatgg taggtaggtt    540
aacataagat gcctccgtga gaggcgaagg ggcggcggga cccgggcctg cccgtatgt    600 gtccttggcg gcctagacta ggccgtcgct gtatggtgag ccccagggag gcggatctgg    660
gcccccagaa ggacacccgc ctggatttgc cccgtagccc ggcccgggcc cctcgggagc    720
agaacagcct tggtgaggtg gacaggaggg gacctcgcga gcagacgcgc gcgccagcga    780
cagcagcccc gccccggcct ctcggagccc ggggggcaga ggctgcggag ccccaggagg    840
gtctatcagc cacagtctct gcatgtttcc aagagcaaca ggaaatgaac acattgcagg    900
ggccagtgtc attcaaagat gtggctgtgg atttcaccca ggaggagtgg cggcaactgg    960
accctgatga gaagatagca tacggggatg tgatgttgga gaactacagc catctagttt   1020
```

```
ctgtggggta tgattatcac caagccaaac atcatcatgg agtggaggtg aaggaagtgg    1080
agcagggaga ggagccgtgg ataatggaag gtgaatttcc atgtcaacat agtccagaac    1140
ctgctaaggc catcaaacct attgatcgga agtcagtcca tcagatttgc tctgggccag    1200
tggtactgag tctaagcact gcagtgaagg agttagtaga aaacagtctg gatgctggtg    1260
ccactaatat tgatctaaag cttaaggact atggagtgga tctcattgaa gtttcagaca    1320
atggatgtgg ggtagaagaa gaaaactttg aaggcttaat ctctttcagc tctgaaacat    1380
cacacatgta agattcaaga gtttgccgac ctaactgaag ttgaaacttt cggttttcag    1440
ggggaagctc tgagctcact gtgtgcactg agcgatgtca ccatttctac ctgccacgcg    1500
ttggtgaagg ttgggactcg actggtgttt gatcacgatg ggaaaatcat ccaggaaacc    1560
ccctaccccc accccagagg gaccacagtc agcgtgaagc agttatttc tacgctacct     1620 gtgcgccata aggaatttca aggaatatt aagaagacgt gcctgcttcc ccttcgcctt     1680
ctgccgtgat tgtcagtttc ctgaggcctc cccagccatg cttcctgtac agcctgcaga    1740
actgtgagtc aattaaacct cttttcttca taaattaaaa aaaaa                    1785

<210> SEQ ID NO 14
<211> LENGTH: 795
<212> TYPE: DNA
<213> ORGANISM: Homo sapiens

<400> SEQUENCE: 14
atgtgtcctt ggcggcctag actaggccgt cgctgtatgg tgagccccag ggaggcggat     60
ctgggccccc agaaggacac ccgcctggat ttgccccgta gcccggcccg ggccctcgg    120 gagcagaaca gccttggtga ggtggacagg aggggacctc gcgagcagac gcgcgcgcca    180
gcgacagcag ccccgccccg gcctctcggg agcgggggg cagaggctgc ggagccccag    240
gagggtctat cagccacagt ctctgcatgt ttccaagagc aacaggaaat gaacacattg    300
caggggccag tgtcattcaa agatgtggct gtggatttca cccaggagga gtggcggcaa    360
ctggaccctg atgagaagat agcatacggg gatgtgatgt ggagaactac agccatcta    420 gtttctgtgg ggtatgatta tcaccaagcc aaacatcatc atggagtgga ggtgaaggaa    480
gtggagcagg gagaggagcc gtggataatg aaggtgaat tccatgtca acatagtcca    540 gaacctgcta aggccatcaa acctattgat cggaagtcag tccatcagat tgctctggg    600 ccagtggtac tgagtctaag cactgcagtg aaggagttag tagaaaacag tctggatgct    660
ggtgccacta atattgatct aaagcttaag gactatggag tggatctcat tgaagtttca    720
gacaatggat gtggggtaga agaagaaaac tttgaaggct taatctcttt cagctctgaa    780
acatcacaca tgtaa                                                     795

<210> SEQ ID NO 15
<211> LENGTH: 769
<212> TYPE: PRT
<213> ORGANISM: Saccharomyces cerevisiae

<400> SEQUENCE: 15

Met Ser Leu Arg Ile Lys Ala Leu Asp Ala Ser Val Val Asn Lys Ile
1               5                   10                  15

Ala Ala Gly Glu Ile Ile Ile Ser Pro Val Asn Ala Leu Lys Glu Met
                20                  25                  30

Met Glu Asn Ser Ile Asp Ala Asn Ala Thr Met Ile Asp Ile Leu Val
        35                  40                  45
```

```
Lys Glu Gly Gly Ile Lys Val Leu Gln Ile Thr Asp Asn Gly Ser Gly
         50                  55                  60

Ile Asn Lys Ala Asp Leu Pro Ile Leu Cys Glu Arg Phe Thr Thr Ser
 65              70                  75                  80

Lys Leu Gln Lys Phe Glu Asp Leu Ser Gln Ile Gln Thr Tyr Gly Phe
                 85                  90                  95

Arg Gly Glu Ala Leu Ala Ser Ile Ser His Val Ala Arg Val Thr Val
            100                 105                 110

Thr Thr Lys Val Lys Glu Asp Arg Cys Ala Trp Arg Val Ser Tyr Ala
            115                 120                 125

Glu Gly Lys Met Leu Glu Ser Pro Lys Pro Val Ala Gly Lys Asp Gly
            130                 135                 140

Thr Thr Ile Leu Val Glu Asp Leu Phe Phe Asn Ile Pro Ser Arg Leu
145                 150                 155                 160

Arg Ala Leu Arg Ser His Asn Asp Glu Tyr Ser Lys Ile Leu Asp Val
                165                 170                 175

Val Gly Arg Tyr Ala Ile His Ser Lys Asp Ile Gly Phe Ser Cys Lys
            180                 185                 190

Lys Phe Gly Asp Ser Asn Tyr Ser Leu Ser Val Lys Pro Ser Tyr Thr
        195                 200                 205

Val Gln Asp Arg Ile Arg Thr Val Phe Asn Lys Ser Val Ala Ser Asn
210                 215                 220

Leu Ile Thr Phe His Ile Ser Lys Val Glu Asp Leu Asn Leu Glu Ser
225                 230                 235                 240

Val Asp Gly Lys Val Cys Asn Leu Asn Phe Ile Ser Lys Lys Ser Ile
            245                 250                 255

Ser Leu Ile Phe Phe Ile Asn Asn Arg Leu Val Thr Cys Asp Leu Leu
            260                 265                 270

Arg Arg Ala Leu Asn Ser Val Tyr Ser Asn Tyr Leu Pro Lys Gly Phe
        275                 280                 285

Arg Pro Phe Ile Tyr Leu Gly Ile Val Ile Asp Pro Ala Ala Val Asp
    290                 295                 300

Val Asn Val His Pro Thr Lys Arg Glu Val Arg Phe Leu Ser Gln Asp
305                 310                 315                 320

Glu Ile Ile Glu Lys Ile Ala Asn Gln Leu His Ala Glu Leu Ser Ala
            325                 330                 335

Ile Asp Thr Ser Arg Thr Phe Lys Ala Ser Ser Ile Ser Thr Asn Lys
        340                 345                 350

Pro Glu Ser Leu Ile Pro Phe Asn Asp Thr Ile Glu Ser Asp Arg Asn
        355                 360                 365

Arg Lys Ser Leu Arg Gln Ala Gln Val Val Glu Asn Ser Tyr Thr Thr
        370                 375                 380

Ala Asn Ser Gln Leu Arg Lys Ala Lys Arg Gln Glu Asn Lys Leu Val
385                 390                 395                 400

Arg Ile Asp Ala Ser Gln Ala Lys Ile Thr Ser Phe Leu Ser Ser Ser
            405                 410                 415

Gln Gln Phe Asn Phe Glu Gly Ser Ser Thr Lys Arg Gln Leu Ser Glu
            420                 425                 430

Pro Lys Val Thr Asn Val Ser His Ser Gln Glu Ala Glu Lys Leu Thr
        435                 440                 445

Leu Asn Glu Ser Glu Gln Pro Arg Asp Ala Asn Thr Ile Asn Asp Asn
450                 455                 460
```

```
Asp Leu Lys Asp Gln Pro Lys Lys Gln Lys Leu Gly Asp Tyr Lys
465                 470                 475                 480

Val Pro Ser Ile Ala Asp Glu Lys Asn Ala Leu Pro Ile Ser Lys
                485                 490                 495

Asp Gly Tyr Ile Arg Val Pro Lys Glu Arg Val Asn Val Asn Leu Thr
            500                 505                 510

Ser Ile Lys Lys Leu Arg Glu Lys Val Asp Asp Ser Ile His Arg Glu
        515                 520                 525

Leu Thr Asp Ile Phe Ala Asn Leu Asn Tyr Val Gly Val Val Asp Glu
    530                 535                 540

Glu Arg Arg Leu Ala Ala Ile Gln His Asp Leu Lys Leu Phe Leu Ile
545                 550                 555                 560

Asp Tyr Gly Ser Val Cys Tyr Glu Leu Phe Tyr Gln Ile Gly Leu Thr
                565                 570                 575

Asp Phe Ala Asn Phe Gly Lys Ile Asn Leu Gln Ser Thr Asn Val Ser
            580                 585                 590

Asp Asp Ile Val Leu Tyr Asn Leu Ser Glu Phe Asp Glu Leu Asn
        595                 600                 605

Asp Asp Ala Ser Lys Glu Lys Ile Ile Ser Lys Ile Trp Asp Met Ser
610                 615                 620

Ser Met Leu Asn Glu Tyr Tyr Ser Ile Glu Leu Val Asn Asp Gly Leu
625                 630                 635                 640

Asp Asn Asp Leu Lys Ser Val Lys Leu Lys Ser Leu Pro Leu Leu Leu
                645                 650                 655

Lys Gly Tyr Ile Pro Ser Leu Val Lys Leu Pro Phe Phe Ile Tyr Arg
            660                 665                 670

Leu Gly Lys Glu Val Asp Trp Glu Asp Glu Gln Glu Cys Leu Asp Gly
        675                 680                 685

Ile Leu Arg Glu Ile Ala Leu Leu Tyr Ile Pro Asp Met Val Pro Lys
    690                 695                 700

Val Asp Thr Leu Asp Ala Ser Leu Ser Glu Asp Glu Lys Ala Gln Phe
705                 710                 715                 720

Ile Asn Arg Lys Glu His Ile Ser Ser Leu Glu His Val Leu Phe
                725                 730                 735

Pro Cys Ile Lys Arg Arg Phe Leu Ala Pro Arg His Ile Leu Lys Asp
            740                 745                 750

Val Val Glu Ile Ala Asn Leu Pro Asp Leu Tyr Lys Val Phe Glu Arg
        755                 760                 765

Cys

<210> SEQ ID NO 16
<211> LENGTH: 859
<212> TYPE: PRT
<213> ORGANISM: Mus musculus

<400> SEQUENCE: 16

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60
```

-continued

```
Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
            115                 120                 125

Ala Ser Val Gly Thr Arg Leu Val Phe Asp His Asn Gly Lys Ile Thr
130                 135                 140

Gln Lys Thr Pro Tyr Pro Arg Pro Lys Gly Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
            195                 200                 205

Gly Lys Arg His Ala Val Val Cys Thr Ser Gly Thr Ser Gly Met Lys
210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
            275                 280                 285

Phe Ser Ser Ser Ile Arg Gly Pro Val Thr Gln Gln Arg Ser Leu Ser
290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Ala Asn
            355                 360                 365

Lys Leu Asn Val Asn Gln Gln Pro Leu Leu Asp Val Glu Gly Asn Leu
370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
            435                 440                 445

Ser Glu Lys Arg Gly Val Leu Ser Ser Tyr Pro Ser Asp Val Ile Ser
450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
```

-continued

```
                485                 490                 495
Leu Ser Ser Thr Ser Ala Gly Ser Glu Glu Phe Ser Thr Pro Glu
            500                 505                 510
Val Ala Ser Ser Phe Ser Ser Asp Tyr Asn Val Ser Ser Leu Glu Asp
            515                 520                 525
Arg Pro Ser Gln Glu Thr Ile Asn Cys Gly Asp Leu Asp Cys Arg Pro
            530                 535                 540
Pro Gly Thr Gly Gln Ser Leu Lys Pro Glu Asp His Gly Tyr Gln Cys
545                 550                 555                 560
Lys Ala Leu Pro Leu Ala Arg Leu Ser Pro Thr Asn Ala Lys Arg Phe
                565                 570                 575
Lys Thr Glu Glu Arg Pro Ser Asn Val Asn Ile Ser Gln Arg Leu Pro
            580                 585                 590
Gly Pro Gln Ser Thr Ser Ala Ala Glu Val Asp Val Ala Ile Lys Met
            595                 600                 605
Asn Lys Arg Ile Val Leu Leu Glu Phe Ser Leu Ser Ser Leu Ala Lys
            610                 615                 620
Arg Met Lys Gln Leu Gln His Leu Lys Ala Gln Asn Lys His Glu Leu
625                 630                 635                 640
Ser Tyr Arg Lys Phe Arg Ala Lys Ile Cys Pro Gly Glu Asn Gln Ala
                645                 650                 655
Ala Glu Asp Glu Leu Arg Lys Glu Ile Ser Lys Ser Met Phe Ala Glu
            660                 665                 670
Met Glu Ile Leu Gly Gln Phe Asn Leu Gly Phe Ile Val Thr Lys Leu
            675                 680                 685
Lys Glu Asp Leu Phe Leu Val Asp Gln His Ala Ala Asp Glu Lys Tyr
690                 695                 700
Asn Phe Glu Met Leu Gln Gln His Thr Val Leu Gln Ala Gln Arg Leu
705                 710                 715                 720
Ile Thr Pro Gln Thr Leu Asn Leu Thr Ala Val Asn Glu Ala Val Leu
                725                 730                 735
Ile Glu Asn Leu Glu Ile Phe Arg Lys Asn Gly Phe Asp Phe Val Ile
            740                 745                 750
Asp Glu Asp Ala Pro Val Thr Glu Arg Ala Lys Leu Ile Ser Leu Pro
            755                 760                 765
Thr Ser Lys Asn Trp Thr Phe Gly Pro Gln Asp Ile Asp Glu Leu Ile
            770                 775                 780
Phe Met Leu Ser Asp Ser Pro Gly Val Met Cys Arg Pro Ser Arg Val
785                 790                 795                 800
Arg Gln Met Phe Ala Ser Arg Ala Cys Arg Lys Ser Val Met Ile Gly
                805                 810                 815
Thr Ala Leu Asn Ala Ser Glu Met Lys Lys Leu Ile Thr His Met Gly
            820                 825                 830
Glu Met Asp His Pro Trp Asn Cys Pro His Gly Arg Pro Thr Met Arg
            835                 840                 845
His Val Ala Asn Leu Asp Val Ile Ser Gln Asn
850                 855
```

<210> SEQ ID NO 17
<211> LENGTH: 932
<212> TYPE: PRT
<213> ORGANISM: Homo sapiens

<400> SEQUENCE: 17

-continued

```
Met Lys Gln Leu Pro Ala Ala Thr Val Arg Leu Leu Ser Ser Ser Gln
  1               5                  10                  15

Ile Ile Thr Ser Val Val Ser Val Val Lys Glu Leu Ile Glu Asn Ser
             20                  25                  30

Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
             100                 105                 110

Ala Ala Asp Asn Phe Ser Thr Gln Tyr Val Leu Asp Gly Ser Gly His
         115                 120                 125

Ile Leu Ser Gln Lys Pro Ser His Leu Gly Gln Gly Thr Thr Val Thr
 130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                 165                 170                 175

Met Ser Phe Gly Ile Leu Lys Pro Asp Leu Arg Ile Val Phe Val His
             180                 185                 190

Asn Lys Ala Val Ile Trp Gln Lys Ser Arg Val Ser Asp His Lys Met
         195                 200                 205

Ala Leu Met Ser Val Leu Gly Thr Ala Val Met Asn Asn Met Glu Ser
210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                 245                 250                 255

Arg Ser Phe Ile Phe Ile Asn Ser Arg Pro Val His Gln Lys Asp Ile
             260                 265                 270

Leu Lys Leu Ile Arg His His Tyr Asn Leu Lys Cys Leu Lys Glu Ser
         275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                 325                 330                 335

Tyr Gly Pro Leu Pro Ser Thr Asn Ser Tyr Glu Asn Asn Lys Thr Asp
             340                 345                 350

Val Ser Ala Ala Asp Ile Val Leu Ser Lys Thr Ala Glu Thr Asp Val
         355                 360                 365

Leu Phe Asn Lys Val Glu Ser Ser Gly Lys Asn Tyr Ser Asn Val Asp
370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                 405                 410                 415

Gly Tyr Gly His Cys Ser Ser Glu Ile Ser Asn Ile Asp Lys Asn Thr
```

-continued

```
                420             425             430
Lys Asn Ala Phe Gln Asp Ile Ser Met Ser Asn Val Ser Trp Glu Asn
            435                 440                 445
Ser Gln Thr Glu Tyr Ser Lys Thr Cys Phe Ile Ser Ser Val Lys His
        450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Glu Ile Ser Ala Asp
                485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
        515                 520                 525
Ser Asn Asn Asn Tyr Pro Ile Pro Glu Gln Met Asn Leu Asn Glu Asp
        530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                565                 570                 575
Ala Ser Ala Leu Phe Val Gln Asp His Arg Pro Gln Phe Leu Ile Glu
            580                 585                 590
Asn Pro Lys Thr Ser Leu Glu Asp Ala Thr Leu Gln Ile Glu Glu Leu
        595                 600                 605
Trp Lys Thr Leu Ser Glu Glu Lys Leu Lys Tyr Glu Glu Lys Ala
        610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Ile Lys Pro
                645                 650                 655
Thr Ser Ala Trp Asn Leu Ala Gln His Lys Leu Lys Thr Ser Leu
            660                 665                 670
Ser Asn Gln Pro Lys Leu Asp Glu Leu Leu Gln Ser Gln Ile Glu Lys
        675                 680                 685
Arg Arg Ser Gln Asn Ile Lys Met Val Gln Ile Pro Phe Ser Met Lys
        690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
                725                 730                 735
Leu Met Thr Ser Lys Thr Glu Val Met Leu Leu Asn Pro Tyr Arg Val
            740                 745                 750
Glu Glu Ala Leu Leu Phe Lys Arg Leu Leu Glu Asn His Lys Leu Pro
        755                 760                 765
Ala Glu Pro Leu Glu Lys Pro Ile Met Leu Thr Glu Ser Leu Phe Asn
        770                 775                 780
Gly Ser His Tyr Leu Asp Val Leu Tyr Lys Met Thr Ala Asp Gln
785                 790                 795                 800
Arg Tyr Ser Gly Ser Thr Tyr Leu Ser Asp Pro Arg Leu Thr Ala Asn
                805                 810                 815
Gly Phe Lys Ile Lys Leu Ile Pro Gly Val Ser Ile Thr Glu Asn Tyr
            820                 825                 830
Leu Glu Ile Glu Gly Met Ala Asn Cys Leu Pro Phe Tyr Gly Val Ala
        835                 840                 845
```

```
Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His His Leu Thr Tyr Leu
                915                 920                 925

Pro Glu Thr Thr
    930

<210> SEQ ID NO 18
<211> LENGTH: 932
<212> TYPE: PRT
<213> ORGANISM: Homo sapiens

<400> SEQUENCE: 18

Met Lys Gln Leu Pro Ala Ala Thr Val Arg Leu Leu Ser Ser Ser Gln
  1               5                  10                  15

Ile Ile Thr Ser Val Val Ser Val Val Lys Glu Leu Ile Glu Asn Ser
             20                  25                  30

Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
```

-continued

```
                275                 280                 285
Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
                355                 360                 365

Leu Phe Asn Lys Val Glu Ser Ser Gly Lys Asn Tyr Ser Asn Val Asp
370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
                420                 425                 430

Lys Asn Ala Phe Gln Asp Ile Ser Met Ser Asn Val Ser Trp Glu Asn
                435                 440                 445

Ser Gln Thr Glu Tyr Ser Lys Thr Cys Phe Ile Ser Ser Val Lys His
                450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
                500                 505                 510

Glu Pro Val Lys Ile Leu Val Pro Glu Lys Ser Leu Pro Cys Lys Val
                515                 520                 525

Ser Asn Asn Asn Tyr Pro Ile Pro Glu Gln Met Asn Leu Asn Glu Asp
530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
                580                 585                 590

Asn Pro Lys Thr Ser Leu Glu Asp Ala Thr Leu Gln Ile Glu Glu Leu
                595                 600                 605

Trp Lys Thr Leu Ser Glu Glu Lys Leu Lys Tyr Glu Glu Lys Ala
                610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Ile Lys Pro
                645                 650                 655

Thr Ser Ala Trp Asn Leu Ala Gln Lys His Lys Leu Lys Thr Ser Leu
                660                 665                 670

Ser Asn Gln Pro Lys Leu Asp Glu Leu Leu Gln Ser Gln Ile Glu Lys
                675                 680                 685

Arg Arg Ser Gln Asn Ile Lys Met Val Gln Ile Pro Phe Ser Met Lys
                690                 695                 700
```

```
Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
            725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
            805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
            850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
            885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His His Leu Thr Tyr Leu
            915                 920                 925

Pro Glu Thr Thr
        930

<210> SEQ ID NO 19
<211> LENGTH: 934
<212> TYPE: PRT
<213> ORGANISM: Homo sapiens

<400> SEQUENCE: 19

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
```

-continued

```
            130                 135                 140
Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
                195                 200                 205

Asp Met Gly Lys Leu Arg Gln Ile Ile Gln Arg Gly Gly Ile Leu Ile
            210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
            275                 280                 285

Phe Glu Leu Thr Thr Phe Asp Phe Ser Gln Tyr Met Lys Leu Asp Ile
            290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
            355                 360                 365

Asp Ala Glu Leu Arg Gln Thr Leu Gln Glu Asp Leu Leu Arg Arg Phe
            370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
            435                 440                 445

Lys Phe Gln Glu Met Ile Glu Thr Thr Leu Asp Met Asp Gln Val Glu
            450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
            530                 535                 540

Gln Lys Asn Gly Val Lys Phe Thr Asn Ser Lys Leu Thr Ser Leu Asn
545                 550                 555                 560
```

```
Glu Glu Tyr Thr Lys Asn Lys Thr Glu Tyr Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
        595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
        915                 920                 925

Arg Ile Lys Val Thr Thr
930

<210> SEQ ID NO 20
<211> LENGTH: 756
<212> TYPE: PRT
<213> ORGANISM: Homo sapiens
```

<400> SEQUENCE: 20

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Val
    370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415
```

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Ser Arg Lys Glu Met Thr Ala Ala Cys Thr Pro
            485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
        530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
            565                 570                 575

Ser Glu Pro Ala Pro Leu Phe Asp Leu Ala Met Leu Ala Leu Asp Ser
        580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
            645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
            675                 680                 685

Gln Tyr Ile Ser Glu Glu Ser Thr Leu Ser Gly Gln Gln Ser Glu Val
        690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
            725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 21
<211> LENGTH: 133
<212> TYPE: PRT
<213> ORGANISM: Homo sapiens

<400> SEQUENCE: 21

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser

-continued

```
                    20                  25                  30
Leu Asp Ala Gly Ala Thr Ser Val Asp Val Lys Leu Glu Asn Tyr Gly
            35                  40                  45

Phe Asp Lys Ile Glu Val Arg Asp Asn Gly Glu Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
            115                 120                 125

Ile Leu Ser Gln Lys
            130

<210> SEQ ID NO 22
<211> LENGTH: 1360
<212> TYPE: PRT
<213> ORGANISM: Homo sapiens

<400> SEQUENCE: 22

Met Ser Arg Gln Ser Thr Leu Tyr Ser Phe Phe Pro Lys Ser Pro Ala
 1               5                  10                  15

Leu Ser Asp Ala Asn Lys Ala Ser Ala Arg Ala Ser Arg Glu Gly Gly
            20                  25                  30

Arg Ala Ala Ala Pro Gly Ala Ser Pro Ser Pro Gly Gly Asp Ala Ala
            35                  40                  45

Ala Trp Ser Glu Ala Gly Pro Gly Pro Arg Pro Leu Ala Arg Ser Ala
 50                  55                  60

Ser Pro Pro Lys Ala Lys Asn Leu Asn Gly Gly Leu Arg Arg Ser Val
 65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
            100                 105                 110

His Pro Phe Asp Gly Thr Phe Ile Arg Glu Lys Gly Lys Ser Val Arg
            115                 120                 125

Val His Val Gln Phe Phe Asp Asp Ser Pro Thr Arg Gly Trp Val Ser
            130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Glu Met
            195                 200                 205

Glu Val Gly Thr Thr Tyr Val Thr Asp Lys Ser Glu Glu Asp Asn Glu
            210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255
```

-continued

```
Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
        290                 295                 300

Thr Gly Asn Gly Ser Leu Lys Arg Lys Ser Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
    370                 375                 380

Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
                405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445

Leu Val Phe Met Lys Gly Asn Trp Ala His Ser Gly Phe Pro Glu Ile
    450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
        515                 520                 525

Gly Asp Pro Ser Glu Asn Tyr Ser Lys Tyr Leu Leu Ser Leu Lys Glu
    530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
        595                 600                 605

Leu Lys Ser Ser Leu Ser Cys Ser Leu Gln Glu Gly Leu Ile Pro Gly
    610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
```

-continued

```
            675                 680                 685
Phe Tyr Leu Lys Lys Cys Leu Ile Asp Gln Glu Leu Leu Ser Met Ala
690                 695                 700
Asn Phe Glu Glu Tyr Ile Pro Leu Asp Ser Asp Thr Val Ser Thr Thr
705                 710                 715                 720
Arg Ser Gly Ala Ile Phe Thr Lys Ala Tyr Gln Arg Met Val Leu Asp
            725                 730                 735
Ala Val Thr Leu Asn Asn Leu Glu Ile Phe Leu Asn Gly Thr Asn Gly
            740                 745                 750
Ser Thr Glu Gly Thr Leu Leu Glu Arg Val Asp Thr Cys His Thr Pro
            755                 760                 765
Phe Gly Lys Arg Leu Leu Lys Gln Trp Leu Cys Ala Pro Leu Cys Asn
            770                 775                 780
His Tyr Ala Ile Asn Asp Arg Leu Asp Ala Ile Glu Asp Leu Met Val
785                 790                 795                 800
Val Pro Asp Lys Ile Ser Glu Val Val Glu Leu Leu Lys Lys Leu Pro
            805                 810                 815
Asp Leu Glu Arg Leu Leu Ser Lys Ile His Asn Val Gly Ser Pro Leu
            820                 825                 830
Lys Ser Gln Asn His Pro Asp Ser Arg Ala Ile Met Tyr Glu Glu Thr
            835                 840                 845
Thr Tyr Ser Lys Lys Lys Ile Ile Asp Phe Leu Ser Ala Leu Glu Gly
            850                 855                 860
Phe Lys Val Met Cys Lys Ile Ile Gly Ile Met Glu Glu Val Ala Asp
865                 870                 875                 880
Gly Phe Lys Ser Lys Ile Leu Lys Gln Val Ile Ser Leu Gln Thr Lys
            885                 890                 895
Asn Pro Glu Gly Arg Phe Pro Asp Leu Thr Val Glu Leu Asn Arg Trp
            900                 905                 910
Asp Thr Ala Phe Asp His Glu Lys Ala Arg Lys Thr Gly Leu Ile Thr
            915                 920                 925
Pro Lys Ala Gly Phe Asp Ser Asp Tyr Asp Gln Ala Leu Ala Asp Ile
            930                 935                 940
Arg Glu Asn Glu Gln Ser Leu Leu Glu Tyr Leu Glu Lys Gln Arg Asn
945                 950                 955                 960
Arg Ile Gly Cys Arg Thr Ile Val Tyr Trp Gly Ile Gly Arg Asn Arg
                965                 970                 975
Tyr Gln Leu Glu Ile Pro Glu Asn Phe Thr Thr Arg Asn Leu Pro Glu
            980                 985                 990
Glu Tyr Glu Leu Lys Ser Thr Lys Lys Gly Cys Lys Arg Tyr Trp Thr
            995                 1000                1005
Lys Thr Ile Glu Lys Lys Leu Ala Asn Leu Ile Asn Ala Glu Glu Arg
            1010                1015                1020
Arg Asp Val Ser Leu Lys Asp Cys Met Arg Arg Leu Phe Tyr Asn Phe
1025                1030                1035                1040
Asp Lys Asn Tyr Lys Asp Trp Gln Ser Ala Val Glu Cys Ile Ala Val
                1045                1050                1055
Leu Asp Val Leu Leu Cys Leu Ala Asn Tyr Ser Arg Gly Gly Asp Gly
                1060                1065                1070
Pro Met Cys Arg Pro Val Ile Leu Leu Pro Glu Asp Thr Pro Pro Phe
            1075                1080                1085
Leu Glu Leu Lys Gly Ser Arg His Pro Cys Ile Thr Lys Thr Phe Phe
            1090                1095                1100
```

```
Gly Asp Asp Phe Ile Pro Asn Asp Ile Leu Ile Gly Cys Glu Glu Glu
1105                1110                1115                1120

Glu Gln Glu Asn Gly Lys Ala Tyr Cys Val Leu Val Thr Gly Pro Asn
            1125                1130                1135

Met Gly Gly Lys Ser Thr Leu Met Arg Gln Ala Gly Leu Leu Ala Val
        1140                1145                1150

Met Ala Gln Met Gly Cys Tyr Val Pro Ala Glu Val Cys Arg Leu Thr
            1155                1160                1165

Pro Ile Asp Arg Val Phe Thr Arg Leu Gly Ala Ser Asp Arg Ile Met
        1170                1175                1180

Ser Gly Glu Ser Thr Phe Phe Val Glu Leu Ser Glu Thr Ala Ser Ile
1185                1190                1195                1200

Leu Met His Ala Thr Ala His Ser Leu Val Leu Val Asp Glu Leu Gly
                1205                1210                1215

Arg Gly Thr Ala Thr Phe Asp Gly Thr Ala Ile Ala Asn Ala Val Val
                1220                1225                1230

Lys Glu Leu Ala Glu Thr Ile Lys Cys Arg Thr Leu Phe Ser Thr His
            1235                1240                1245

Tyr His Ser Leu Val Glu Asp Tyr Ser Gln Asn Val Ala Val Arg Leu
        1250                1255                1260

Gly His Met Ala Cys Met Val Glu Asn Glu Cys Glu Asp Pro Ser Gln
1265                1270                1275                1280

Glu Thr Ile Thr Phe Leu Tyr Lys Phe Ile Lys Gly Ala Cys Pro Lys
                1285                1290                1295

Ser Tyr Gly Phe Asn Ala Ala Arg Leu Ala Asn Leu Pro Glu Glu Val
            1300                1305                1310

Ile Gln Lys Gly His Arg Lys Ala Arg Glu Phe Glu Lys Met Asn Gln
        1315                1320                1325

Ser Leu Arg Leu Phe Arg Glu Val Cys Leu Ala Ser Glu Arg Ser Thr
    1330                1335                1340

Val Asp Ala Glu Ala Val His Lys Leu Leu Thr Leu Ile Lys Glu Leu
1345                1350                1355                1360

<210> SEQ ID NO 23
<211> LENGTH: 389
<212> TYPE: PRT
<213> ORGANISM: Homo sapiens

<400> SEQUENCE: 23

Met Ala Gln Pro Lys Gln Glu Arg Val Ala Arg Ala Arg His Gln Arg
1               5                   10                  15

Ser Glu Thr Ala Arg His Gln Arg Ser Glu Thr Ala Lys Thr Pro Thr
            20                  25                  30

Leu Gly Asn Arg Gln Thr Pro Thr Leu Gly Asn Arg Gln Thr Pro Arg
        35                  40                  45

Leu Gly Ile His Ala Arg Pro Arg Arg Ala Thr Thr Ser Leu Leu
    50                  55                  60

Thr Leu Leu Leu Ala Phe Gly Lys Asn Ala Val Arg Cys Ala Leu Ile
65                  70                  75                  80

Gly Pro Gly Ser Leu Thr Ser Arg Thr Arg Pro Leu Thr Glu Pro Leu
                85                  90                  95

Gly Glu Lys Glu Arg Arg Glu Val Phe Phe Pro Pro Arg Pro Glu Arg
            100                 105                 110

Val Glu His Asn Val Glu Ser Ser Arg Trp Glu Pro Arg Arg Arg Gly
```

```
                115                 120                 125
Ala Cys Gly Ser Arg Gly Gly Asn Phe Pro Ser Pro Arg Gly Gly Ser
            130                 135                 140

Gly Val Ala Ser Leu Glu Arg Ala Glu Asn Ser Ser Thr Glu Pro Ala
145                 150                 155                 160

Lys Ala Ile Lys Pro Ile Asp Arg Lys Ser Val His Gln Ile Cys Ser
                165                 170                 175

Gly Pro Val Val Pro Ser Leu Arg Pro Asn Ala Val Lys Glu Leu Val
            180                 185                 190

Glu Asn Ser Leu Asp Ala Gly Ala Thr Asn Val Asp Leu Lys Leu Lys
        195                 200                 205

Asp Tyr Gly Val Asp Leu Ile Glu Val Ser Gly Asn Gly Cys Gly Val
    210                 215                 220

Glu Glu Glu Asn Phe Glu Gly Phe Thr Leu Lys His His Thr Cys Lys
225                 230                 235                 240

Ile Gln Glu Phe Ala Asp Leu Thr Gln Val Glu Thr Phe Gly Phe Arg
                245                 250                 255

Gly Glu Ala Leu Ser Ser Leu Cys Ala Leu Ser Asp Val Thr Ile Ser
            260                 265                 270

Thr Cys Arg Val Ser Ala Lys Val Gly Thr Arg Leu Val Phe Asp His
        275                 280                 285

Tyr Gly Lys Ile Ile Gln Lys Thr Pro Tyr Pro Arg Pro Arg Gly Met
    290                 295                 300

Thr Val Ser Val Lys Gln Leu Phe Ser Thr Leu Pro Val His His Lys
305                 310                 315                 320

Glu Phe Gln Arg Asn Ile Lys Lys Lys Arg Ala Cys Phe Pro Phe Ala
                325                 330                 335

Phe Cys Arg Asp Cys Gln Phe Pro Glu Ala Ser Pro Ala Met Leu Pro
            340                 345                 350

Val Gln Pro Val Glu Leu Thr Pro Arg Ser Thr Pro His Pro Cys
        355                 360                 365

Ser Leu Glu Asp Asn Val Ile Thr Val Phe Ser Ser Val Lys Asn Gly
    370                 375                 380

Pro Gly Ser Ser Arg
385

<210> SEQ ID NO 24
<211> LENGTH: 264
<212> TYPE: PRT
<213> ORGANISM: Homo sapiens

<400> SEQUENCE: 24

Met Cys Pro Trp Arg Pro Arg Leu Gly Arg Cys Met Val Ser Pro
 1               5                  10                  15

Arg Glu Ala Asp Leu Gly Pro Gln Lys Asp Thr Arg Leu Asp Leu Pro
                20                  25                  30

Arg Ser Pro Ala Arg Ala Pro Arg Glu Gln Asn Ser Leu Gly Glu Val
            35                  40                  45

Asp Arg Arg Gly Pro Arg Glu Gln Thr Arg Ala Pro Thr Ala Ala
        50                  55                  60

Pro Pro Arg Pro Leu Gly Ser Arg Gly Ala Glu Ala Glu Pro Gln
65                  70                  75                  80

Glu Gly Leu Ser Ala Thr Val Ser Ala Cys Phe Gln Glu Gln Gln Glu
                85                  90                  95
```

```
Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Glu Asn Phe Glu Gly Leu Ile Ser
                245                 250                 255

Phe Ser Ser Glu Thr Ser His Met
            260

<210> SEQ ID NO 25
<211> LENGTH: 264
<212> TYPE: PRT
<213> ORGANISM: Homo sapiens

<400> SEQUENCE: 25

Met Cys Pro Trp Arg Pro Arg Leu Gly Arg Arg Cys Met Val Ser Pro
  1               5                  10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205
```

-continued

```
Ala Val Lys Glu Leu Val Glu Asn Ser Leu Asp Ala Gly Ala Thr Asn
        210                 215                 220
Ile Asp Leu Lys Leu Lys Asp Tyr Gly Val Asp Leu Ile Glu Val Ser
225                 230                 235                 240
Asp Asn Gly Cys Gly Val Glu Glu Glu Asn Phe Glu Gly Leu Ile Ser
                245                 250                 255
Phe Ser Ser Glu Thr Ser His Met
                260
```